(12) United States Patent
Tamerler-Behar et al.

(10) Patent No.: US 11,492,382 B2
(45) Date of Patent: Nov. 8, 2022

(54) CHIMERIC PEPTIDES WITH AN ANTIMICROBIAL DOMAIN AND AN INORGANIC BINDING DOMAIN

(71) Applicant: University of Kansas, Lawrence, KS (US)

(72) Inventors: Candan Tamerler-Behar, Lawrence, KS (US); Emily Caitlyn Wisdom, Albuquerque, NM (US); Kyle Boone, Bonner Springs, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 16/640,662

(22) PCT Filed: Aug. 21, 2018

(86) PCT No.: PCT/US2018/047366
§ 371 (c)(1),
(2) Date: Feb. 20, 2020

(87) PCT Pub. No.: WO2019/040517
PCT Pub. Date: Feb. 28, 2019

(65) Prior Publication Data
US 2020/0369734 A1 Nov. 26, 2020

Related U.S. Application Data

(60) Provisional application No. 62/547,996, filed on Aug. 21, 2017.

(51) Int. Cl.
*C07K 14/47* (2006.01)
*C12N 15/62* (2006.01)

(52) U.S. Cl.
CPC .............. *C07K 14/47* (2013.01); *C12N 15/62* (2013.01); *C07K 2317/24* (2013.01); *C07K 2319/02* (2013.01); *C07K 2319/03* (2013.01)

(58) Field of Classification Search
CPC .................................................. C07K 2319/30
USPC ........................................................ 435/69.7
See application file for complete search history.

(56) References Cited

U.S. PATENT DOCUMENTS

2007/0261775 A1  11/2007 Cunningham et al.
2015/0119334 A1* 4/2015 Ben-Gurion ..... G01N 33/54393
                                                      514/16.7

FOREIGN PATENT DOCUMENTS

WO   WO-2009/055313      4/2009
WO   WO-201 3/183048     12/2013

OTHER PUBLICATIONS

Kwok et al., GFP-labelled Rubisco and aspartate aminotransferase are present in plastid stromules and traffic between plastids. Journal of Experimental Botany, vol. 55, No. 397, pp. 595±604, Mar. 2004.*
Yucesoy et al., Chimeric Peptides as Implant Functionalization Agents for Titanium Alloy Implants with Antimicrobial Properties. JOM (1989) . Apr. 2015;67(4):754-766.*
International Preliminary Report on Patentability issued on PCT/US2018/047366 dated Mar. 5, 2020, 8 pages.
International Search Report and Written Opinion on PCT/US2018/047366 dated Jan. 28, 2019, 12 pages.
Supplementary Partial European Search Report mailed in EP 18848605.4 dated Jun. 15, 2021 (16 pages).
Yucesoy Deniz, et al., "Chimeric Peptides as Implant Functionalization Agents for Titanium Alloy Implants with Antimicrobial Properties," Journal of Metals, vol. 67, No. 4, pp. 754-766 (Mar. 7, 2015).
Wisdom et al. Controlling the Biomimetic Implant Interface: Modulating Antimicrobial Activity by Spacer Design. Journal of molecular and engineering materials. Mar. 2016. vol. 4. No. 16, Article 1640005. (Author's Manuscript pp. 1-25).
Chandler et al., "Targeting Tumor Cells Via EGF Receptors: Selective Toxicity of an HBEGF-Toxin Fusion Protein," Int. J. Cancer (78):106-111 (1998).

* cited by examiner

*Primary Examiner* — Sheridan Swope
(74) *Attorney, Agent, or Firm* — Foley & Lardner LLP

(57) ABSTRACT

Provided in this disclosure are chimeric peptides that include a spacer domain, the spacer domain itself, substrates (e.g., implants) coated with the chimeric peptides, and methods for making and using the coated substrates.

3 Claims, 13 Drawing Sheets

Specification includes a Sequence Listing.

US 11,492,382 B2

CHIMERIC PEPTIDES WITH AN ANTIMICROBIAL DOMAIN AND AN INORGANIC BINDING DOMAIN

CROSS-REFERENCE TO RELATED APPLICATIONS

This application is a U.S. National Phase Application under 35 U.S.C. § 371 of International Application No. PCT/US2018/047366, filed on Aug. 21, 2018, which claims the benefit of priority to U.S. Provisional Patent Application No. 62/547,996, filed on Aug. 21, 2017, the entire disclosure of each of which is herein incorporated by reference for any and all purposes.

U.S. GOVERNMENT RIGHTS

This invention was made with government support under AR062249-03 awarded by the National Institutes of Health. The government has certain rights in the invention.

BACKGROUND

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which the present technology pertains.

Bone and joint implants have revolutionized the healthcare of aging patients whose life expectancy has been increasing.[1] Implants have been intensively used during the last 40 years in treating bone and joint degeneration, neoplasms, trauma and inflammation.[1] Titanium and titanium alloys are used as implant biomaterials due to their biocompatibility, mechanical strength, and noncorrosive properties.[2-5] However, nosocomial microbial attachment to the implant surface can result in infection and inflammation with implant loosening that requires surgical revision. In the first hours following surgery the implant surface is most vulnerable to bacterial colonization and the bacterial pathogens are also most susceptible to antimicrobial treatment.[6,7] With time, bacteria populations multiply and cooperate to form biofilms that function as natural barriers against antibiotic effectiveness.[8] Treatment for infection of this type is difficult and the revision surgery is more complex, adding to patient morbidity and overall health care costs. Despite improvements in implant technology including prophylactic therapy, most implant failures can be attributed to either infection or aseptic loosening resulting from poor integration with host tissue.[9,10] Failure requiring revision surgery is caused by infection in 7.5% of total hip arthroplasty (THA) and 14.8% of total knee arthroplasty (TKA) and by aseptic loosening in 55.2% of THA and 29.8% of TKA.[11] Immediate prevention of bacterial attachment on the implant surface is critical in prevention of infection related failure. However, host cell attachment and viability at the interface is also critical to host bone integration to prevent implant loosening. The challenge is to prevent bacterial colonization on the implant surface while not negatively affecting host cell response that could lead to poor integration of the implant material with the host.

Multiple strategies have been developed with the aim of eliminating microbial attachment on the implant surface. Among them, the use of antibiotics has been commonly employed in daily practice. For example, vancomycin powder is commonly used in posterior spinal wounds and has been shown to decrease surgical site infection. However, the rise of antibiotic resistance is lately becoming a major concern in dealing with bacteria, which also led to an increase in efforts to find alternative strategies.[2-5] Silver, polyethylene glycol (PEG), or quaternary ammonia-based compounds (QACs) have been among the well-studied examples to provide the antimicrobial property by attaching them to the biomaterials using covalent chemical bonds.[12-17] Another strategy is to improve the antibacterial properties of metals by doping them with elements such as bismuth and zinc.[18,19] While promising, chemistry based immobilizations require complex steps, which may be not favorable within biological environment due to their harshness. Additionally, uniform coatings where bioactivity is both preserved and homogenously distributed throughout the biomaterial surface following their coupling onto the biomaterials are challenging to obtain.

SUMMARY

Provided are chimeric peptides comprising a spacer domain, the spacer domain, substrates (e.g., implants) coated with the chimeric peptides, and methods for making and using the coated substrates.

BRIEF DESCRIPTION OF THE DRAWINGS

Illustrative embodiments of the invention will hereafter be described with reference to the accompanying drawings.

DETAILED DESCRIPTION

Figure 1:
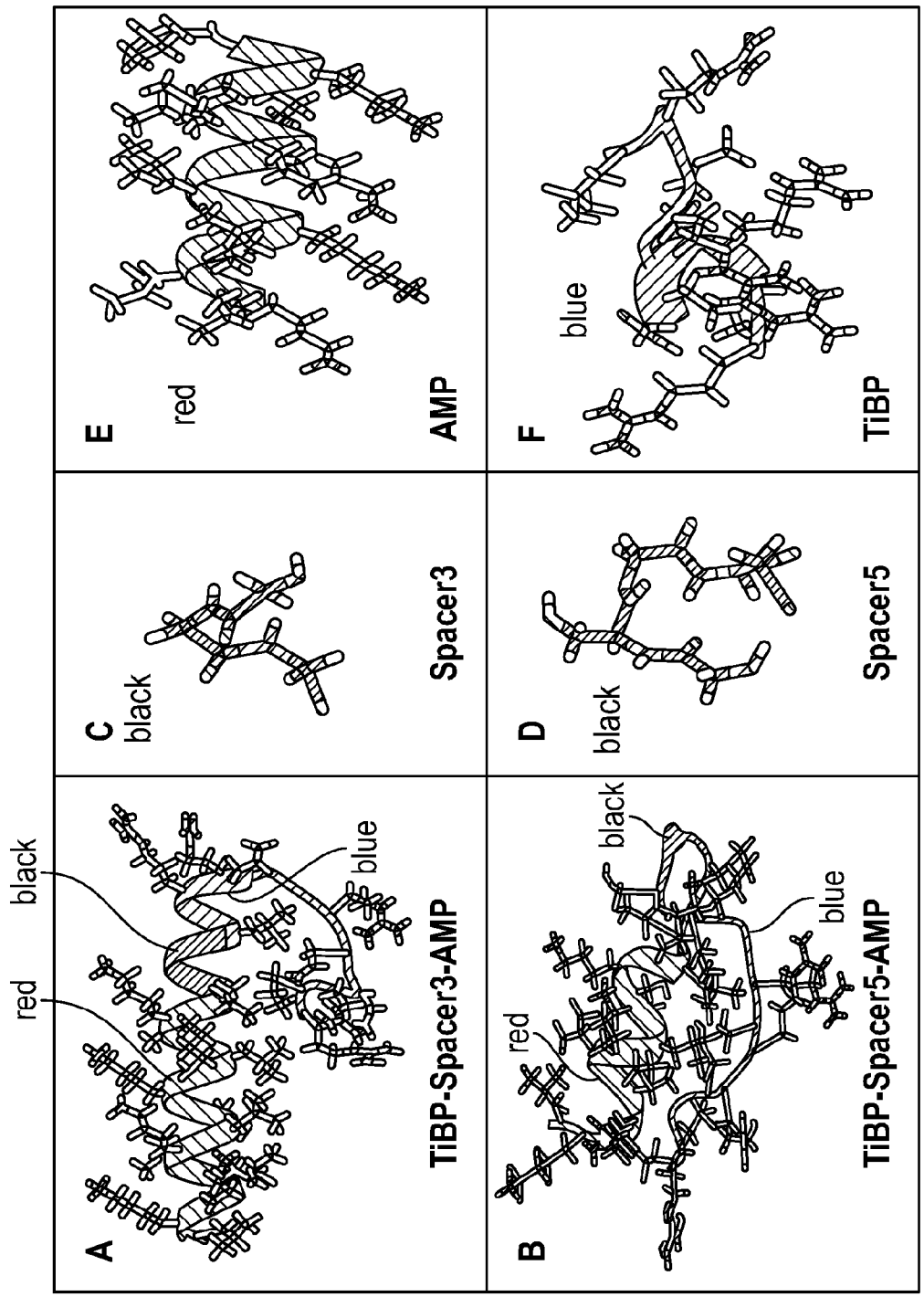
FIG. 1 provides lowest energy structures modeled in solution for A) TiBP-Spacer3-AMP chimeric peptide; B) TiBP-Spacer5-AMP chimeric peptide; C) Spacer3 (GGG) (SEQ ID NO: 1); D) Spacer5 (GSGGG) (SEQ ID NO: 2); E) antimicrobial peptide (AMP); F) titanium binding peptide (TiBP). The peptide backbone is represented as a ribbon to show secondary structure for peptides with side chains represented by full atoms. TiBP domains, spacer domains, and AMP domains are designated with blue-, black-, and red-shading, respectively. The TiBP-Spacer3-AMP (A) has an alpha helix feature beginning with the AMP domain and preserved through Spacer3, whereas TiBP-Spacer5-AMP (B) has a shorter alpha helix ending at Spacer5. Both functional domains, AMP (E) and TiBP (F) have alpha helix secondary structure, with a stronger prominence in the AMP domain.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The present technology is directed to chimeric peptides comprising a spacer domain, the spacer domain itself, substrates (e.g., implants) coated with the chimeric peptides, and methods for making and using the coated substrates.

In one aspect, the present disclosure provides a chimeric peptide. The chimeric peptide comprises an inorganic binding domain, an antimicrobial domain, and a spacer domain between the inorganic binding domain and the antimicrobial domain. The chimeric peptide is a multifunctional (e.g., bifunctional) single-chain peptide which joins the inorganic binding domain and the antimicrobial domain via the spacer domain. The chimeric peptide is relatively short when compared to a biological protein. At least some embodiments of the chimeric peptides (due at least in part to the particular spacer domains within the chimeric peptides) are capable of providing implant surfaces with a fast-acting, broad-spectrum antimicrobial function, thereby preventing bacterial attachment and biofilm formation, while maintaining implant integration with a host tissue. Specifically, at least some embodiments allow the retention of the antimicrobial peptide (AMP) secondary structural features responsible for the antimicrobial activity without jeopardizing the implant self-assembling domain of the peptide. At least some embodiments of the spacer domains induce enough structural alterations in the chimeric peptides to be more effectively displayed at the bio-materials interfaces, leading to improved antimicrobial function and favorable host cell response.

As noted above, the chimeric peptide comprises an antimicrobial domain. The antimicrobial domain is an amino acid sequence selected to exhibit antimicrobial activity, e.g., against selected bacteria. The amino acid sequence may be that corresponding to an antimicrobial peptide (AMP). Thus, the term "AMP" may be used in the present disclosure to refer to the antimicrobial domain of the chimeric peptide. AMPs are a known class of peptides which are abundant in nature and employed as natural innate immune system defense fighters. AMPs are fast-acting antimicrobial agents that are effective against a broad spectrum of grampositive bacteria, gram-negative bacteria, viruses and fungi.[20-22] A variety of AMPs may be used, naturally-occurring peptides, naturally-inspired peptides, and rationally-designed synthetic peptides. In embodiments, AMPs exhibiting antimicrobial activity against bacteria associated with clinical implant infections may be used, e.g., S. mutans and S. epidermidis, S. aureus, MRSA. Other clinically relevant strains for dental and orthopedic implants may be used. An illustrative AMP having such antimicrobial activity has the sequence shown in Table 1 (see Examples section).

The chimeric peptide also comprises an inorganic binding domain. The inorganic binding domain is an amino acid sequence selected to attach and self-assemble on an inorganic surface. The amino acid sequence may be that corresponding to an inorganic binding peptide. Such peptides are a known class of peptides which may be identified using combinatorial biology based molecular libraries, e.g., phage and cell surface display libraries. These genome based screening processes provide candidates that can interact with the inorganic substrates building upon molecular recognition. Due to phenotype-genotype-based relations obtained for inorganic materials throughout the combinatorial biology-based selection process, these peptides are generally referred as genetically engineered peptide for inorganics (GEPIs). GEPIs exhibit an ability to use molecular recognition to self-assemble active peptide-based agents selectively on a variety of inorganic materials including titanium implants.[27,28] For example, there are several titanium binding peptides (TiBP) that assemble onto the titanium surface with high affinity appropriate for the surface of titanium and titanium alloy-based implants.[24,25] Inorganic binding peptides capable of attaching and self-assembling on a variety of inorganic surfaces may be used, e.g., various grades of titanium (Grade I, II, III, IV), titanium alloys, zirconia. In addition to metallic surfaces, mineral surfaces such as various calcium phosphate mineral phases [2, 3], glass surfaces such as quartz can be used [4-7] and polymers such as polypropylene, acrylic polyer, and polyurethane (or a combination of any two or more thereof) may be used [8]. An illustrative titanium binding peptide is a titanium binding peptide having the sequence shown in Table 1 (see Examples section).

The chimeric peptide also comprises the spacer domain—an amino acid sequence that connects the inorganic binding domain to the antimicrobial domain. The amino acid sequence of the spacer domain is selected to segregate and isolate the antimicrobial domain from the rest of the chimeric peptide such that its secondary structure features providing its antimicrobial activity are retained (i.e., as compared to the antimicrobial domain not bound to the spacer domain). Confirmation of retention of antimicrobial activity may be determined by comparing the minimum inhibitory concentration (MIC) of the chimeric peptide to the MIC of the isolated antimicrobial peptide of the chimeric peptide as described in the Examples section, below. A MIC of the chimeric peptide which is within ±1 fold/100% of the MIC of the isolated antimicrobial peptide may indicate retention of antimicrobial activity.

Physical chemical characteristics which may ensure retention of native secondary structure features of the antimicrobial domain and thus, its antimicrobial activity, include one or more of the following: The spacer domain amino acid sequence may be selected such that the chimeric peptide exhibits a relatively short α-helix feature within the chimeric peptide, up to about 20 amino acids, up to about 15 amino acids, up to about 10 amino acids, etc. The spacer domain amino acid sequence may be selected to produce a backbone bend in the chimeric peptide to prevent formation of an extended α-helix feature across the chimeric peptide. Ramachandran plots may be used to evaluate the α-helix features of the chimeric peptide as described in the Examples section, below. The spacer domain amino acid sequence may be selected to optimize (e.g., maximize) the percentage of helix frequency over either a four or five amino acid average in the chimeric peptide. The percentage of helix frequency may be determined using the "rule induction method" as described in the Examples section, below. The spacer amino acid sequence may be selected to increase (e.g., maximize) the amount of non-helical features in the chimeric peptide, such as β sheets, random coils, irregular coils, or a combination of any two or more thereof. Circular dichroism analysis may be used to evaluate the secondary structures of the chimeric peptide as described in the Examples section, below.

The spacer amino acid sequence may be composed of a relatively few number of amino acids. The number of amino acids may be less than 10, including spacer amino acid sequences having, e.g., 9, 8, 7, 6, or 5 amino acids. The amino acids of the spacer amino acid may be selected from any naturally occurring or synthetic amino acid. The genetic algorithm described below provides a way of ranking spacers so that non-performing collections of amino acids can be avoided. An illustrative spacer amino acid sequence is Spacer5 shown in Table 1 (see Example 1). An illustrative chimeric peptide comprising Spacer5 is TiBP-Spacer5-AMP having the sequence also shown in Table 1.

Self-aggregating spacers may be used alone or combined in series with other spacers to produce multi-domain peptides (more than two) in a single polypeptide chain where each individual domain retains its activity. Aggregation mechanisms include disulfide bonds, hydrophobic interactions, charged interactions, pi-pi bond stacking, and hydrogen bonding such as in beta sheet stacking/aggregation observed in naturally occurring fibrils. Examples of self-aggregating spacer pairs (inspired by theta defensin [9]—aggregation through di-sulfide bonds): Defensin Spacer1: GVCRCICTR (SEQ ID NO: 3) and Defensin Spacer 2: GFCRCLCRR (SEQ ID NO: 4) and (inspired by MAXI [10-12]—aggregation through charge repulsion and hydrophobic interactions) MAXI Spacer 1: VKVKVKVKV (SEQ ID NO: 5) and MAXI Spacer 2: TKVKVKVKV (SEQ ID NO: 6).

The chimeric peptides may be characterized by a variety of properties, e.g., minimum inhibitory concentration (MIC) and minimum bactericidal concentration (MBC). Similarly, the spacer domains may be characterized as providing chimeric peptides having such properties. Both MIC and MBC values may be referenced with respect to specific bacteria. These values may be measured according to the techniques and under the conditions described in the Example, below.

The antimicrobial nature of the chimeric peptides may also be quantified by comparing MIC values to those for a comparative chimeric peptide. A comparative chimeric peptide may include the same inorganic binding domain and the same antimicrobial domain as the chimeric peptide, but a different spacer domain as compared to the chimeric peptide. In embodiments, the different spacer domain is Spacer3, having the amino acid sequence shown in Table 1 (Example). In embodiments, the chimeric peptide exhibits a MIC which is less (e.g., at least 2 times lower, at least 3 times lower, at least 5 times lower, etc.) than that of a comparative chimeric peptide comprising spacer amino acid sequence Spacer3.

The antimicrobial properties of the chimeric peptides may also be quantified by the percent surface coverage of specific bacteria on a specific inorganic substrate coated with the chimeric peptide as compared to a control sample (e.g., the bare, uncoated inorganic substrate). The inorganic substrate may comprise any of the inorganic surfaces described above. The inorganic substrate/surface may be configured as a medical implant. By "medical implant" or "implant" it is meant a device configured to contact a biological structure (e.g., organ, tissue, bone, etc.) of an organism such as a mammal (e.g., a human) and to replace, support, or enhance that structure. The type of implant is not particularly limited. Percent surface coverages may be measured according to the techniques and under the conditions described in the Examples section, below. The chimeric peptide may exhibit a percent surface coverage of selected bacteria when coated on a selected inorganic substrate which is at least 5 times less than that of a control sample. This includes percent surface coverages which are at least 10 times less, at least 15 times less, at least 20 times less, at least 25 times less, at least 30 times less, at least 35 times less, or at least 50 times less.

The chimeric peptides (and spacer domains forming such chimeric peptides) may also be characterized by their ability to promote host cell attachment, spreading and viability. A variety of host cells may be used, e.g., a fibroblast. Host cell attachment, spreading and viability may be measured according to the techniques and under the conditions described in the Examples section, below. In embodiments, the chimeric peptide when coated on a selected inorganic substrate supports greater host cell viability (e.g., at least 40% greater, at least 45% greater, or at least 50% greater) of a selected host cell as compared to a control sample (e.g., the bare, uncoated inorganic substrate).

It is to be understood that the spacer domains and their corresponding amino acid sequences as described above are also encompassed by the present disclosure.

The chimeric peptides and spacer domains may be manufactured using known techniques, e.g., solid phase peptide synthesis.

Compositions comprising any of the disclosed chimeric peptides (or the spacer domains) are also provided. Such compositions may comprise a solvent (e.g., water) and one or more additives, e.g., buffer, growth factor, drug, etc.

Coatings comprising any of the disclosed chimeric peptides are also provided. Such a coating may comprise a layer of the chimeric peptide bound to a surface of an inorganic substrate, e.g., any of the inorganic substrates described above configured as an implant. The coated implants are also provided. Methods of making and using the coated implants are also provided. A method of making a coated implant may comprise contacting a surface of an implant with an aqueous solution comprising any of the disclosed chimeric peptides for a period of time to bind the chimeric peptides to the surface to form a coating thereon. A method of using a coated implant may comprise providing the coated implant and inserting the coated implant into a mammal.

EXAMPLES

Example 1. Design and Characterization of Novel Spacer Designs

Experimental

Chimeric Peptide Design

The TiBP and AMP domains used were those previously described.[24,25,30,31] Briefly, TiBP was selected by screening a bacterial surface display system, FliTrx (Invitrogen, Carlsbad, Calif.) against a titanium surface.[27-29] After four rounds of biopanning, 60 clones were selected and characterized based on their surface binding affinity using fluorescence microscopy techniques. The strongest binding sequence determined through these experiments was used in the chimeric peptide to bind it to the titanium surface, thereby anchoring the chimeric peptide. A novel spacer, Spacer5 was designed as an elongated link, joining TiBP with AMP to form the chimeric peptide, TiBP-Spacer5-AMP. TiBP-Spacer5-AMP was synthesized using solid phase peptide synthesis by KanPro (Lawrence, Kans.). Physical chemical data including molecular weight, isoelectric point, charge and GRand AVerage of hydropathY (GRAVY) scores based on amino acid sequences for AMP, TiBP, TiBP-Spacer3-

AMP, and TiBPSpacer5-AMP were obtained using the ExPasy Proteonomics Server.[32]

Molecular Structure Modeling

To understand how the secondary structure of the chimeric peptides changes in solution depending on the spacer sequence, we generated ensembles of 1,000 likely structures using the PyRosetta project software and identified secondary structures with the DSSP program.[33,34] Structure generation is stochastic using a knowledge-based energy scoring function. An ensemble of structures was generated for each full chimeric peptide and each peptide domain to sample likely structural variations. Ramachandran plots were generated for the lowest energy structures for TiBP-Spacer3-AMP and TiBPSpacer5-AMP structures. Chimera Software version 1.9 from University of California at San Francisco was used to visualize the structures.[35]

Antimicrobial "Rule Induction" Method

A "rule induction" method was used to correlate the generated secondary structures with antimicrobial function. Rule induction is a data mining approach to learn associations between paired sets of data made of sets of cases. Paired data is the computationally generated structure decoys for both chimeric AMPs and AMPs paired with the minimum inhibitory concentration (MIC) of the peptides in solution.[1,24] Each structural decoy represents a single case in a set of cases. Given a list of cases where each case has a list of features and a selected outcome, rough-set theory approaches rule induction by looking for features which apply to the maximum number of cases and are selective for the selected outcome.[36] For our project, the cases are structure decoys and the list of features are the secondary structure features found. The paired distinct outcome is the MIC result from the in-solution assay. The rough set theory implementation is based on MLEM2.[37] Two secondary structure features, 4-amino-acid right-handed alpha helices and 5-amino-acid alpha helices were key features for rules.[24] These rules associated with strong antimicrobial activity for the bacteria tested (S. epidermidis and S. mutans). The secondary structure feature frequencies of these two rules were compared against TiBP-Spacer3-AMP and TiBP-Spacer5-AMP. Higher frequencies of these secondary structure features associate with stronger antimicrobial activity.

Circular Dichroism (CD) Analysis

A solution containing 50 µM TiBP-Spacer5-AMP in phosphate buffered saline (PBS) at pH 7.4 was prepared for circular dichroism (CD) analysis. The spectrum is the average of four scans from 190-239 nm using a Jasco J-810 spectrometer (Easton, Md.). Appropriate background buffer subtraction was performed and the instrument carefully calibrated. The averaged spectrum was subtracted from background and smoothed with the Savitzky-Golay algorithm. The spectrum was transformed for mean residue ellipticity in degrees·cm$^2$/dmol. Two methods were used to estimate the secondary structure features from the CD spectra. The CAPITO method makes a comparison to reference spectra for helix ($\alpha$-helix, $3_{10}$-helix and $\pi$-helix), $\beta$-strands ($\beta$-sheets, $\beta$-bridge) and irregular secondary structures (bonded turns, bends and loops) using a liner regression method.[38] The Raussens method is a concentration-independent estimation of $\alpha$-helix, $\beta$-sheets and irregular secondary structure proportions.[39]

Bacterial Maintenance and Culturing

The antimicrobial activity of TiBP-Spacer5-AMP was evaluated against two bacterial strains, S. mutans (American Type Culture Collection (ATCC) 25175, Manassas, Va.) and S. epidermidis (ATCC 29886). S. mutans cultures were prepared using Brain Heart Infusion Broth (BHI, BD Difco, Franklin Lakes, N.J.) and S. epidermidis using Nutrient Broth (NB, BD Difco) according to ATCC protocols. Bacterial pellets obtained from ATCC were rehydrated in appropriate media of which several drops were used to streak either BHI or NB agar plates. Bacteria streaked agar plates were subsequently incubated for 24 h. Agar plates and cultures were incubated at 37° C. in the presence of 5% $CO_2$-supplemented atmosphere for S. mutans and in aerobic atmosphere and 200 rpm shaking for S. epidermidis. Overnight cultures were made by aseptically transferring a single-colony forming unit (CFU) into 10 mL of appropriate broth media followed by incubation in appropriate conditions for 16 h. Bacteria from overnight cultures were used to inoculate fresh media and grown to mid-log phase.

Antimicrobial Activity in Solution

The MIC of TiBP-Spacer5-AMP against S. mutans and S. epidermidis in solution was evaluated in 96 well plates (Corning Costar 3370, Corning, N.Y.) spectrophotometrically over a period of 24 h by obtaining a measurement for the optical density at 600 nm (OD600) every two hours. Optical density at 600 nm was measured using a Cytation3 microplate reader (Bio Tek Instruments, Winooski, Vt.). Bacteria grown to mid-log phase at a density of 107 CFU/mL were cultured at appropriate growth conditions in appropriate broth media only as a control or in broth media containing a range from 5-70 µM of TiBP-Spacer5-AMP for S. mutans and 1-10 µM for S. epidermidis. The OD600 measurements obtained, relating optical density to bacteria CFUs/mL, were plotted versus time to generate standard growth curves. The minimum concentration of TiBP-Spacer5-AMP at which no increase in optical density measurement, corresponding to no bacterial growth occurring was designated as the MIC. AlamarBlue assay (Invitrogen, Carlsbad, Calif.) was used for determination of a minimum bactericidal concentration of TiBP-Spacer5-AMP. Bacteria in broth media only and with the TiBPSpacer5-AMP concentrations described in the MIC experiments were prepared in 96 well plates. AlamarBlue reagent was added to experimental wells and incubated for two hours at 37° C. Experimental wells were observed and evaluated for color change. Wells corresponding to concentrations of TiBP-Spacer5-AMP where no color change occurred were determined to have bactericidal concentrations of the chimeric peptide.

Titanium Surface Preparation

Two surfaces, 99% pure titanium foil (Alfa Aesar 43677, Ward Hill, Mass.) and titanium implant discs cut from standard rods used in posterior lumbar surgery (University of Kansas Medical Center Department of Neurosurgery, Kansas City, Kans.) were used for evaluation of TiBP-Spacer5-AMP biocoating antimicrobial activity. Titanium foils were cut into squares measuring 0.5 mm thick×1 cm×1 cm and 6 mm diameter implant rods were cut by the University of Kansas Medical Center Department of Neurosurgery with a standard orthopedic surgical rod cutter into 3 mm long disc segments. Surfaces were sterilized by soaking overnight in 70% bleach, followed by sonication for 15 min in each 1:1 acetone:methanol, isopropanol and filtered deionized water, dried under UV light in a biosafety cabinet and then autoclaved.

Chimeric Peptide Coating on Surfaces

Sterilized titanium surfaces were transferred to sterile 24 well plates (Costar 3738) with the bactericidal concentrations (60 µM for S. mutans and 10 µM for S. epidermidis) of TiBP-Spacer5-AMP dissolved in PBS at pH 7.4 and incubated at 37° C., constant agitation (200 rpm) for 4 h.[24] Following incubation substrates were washed twice by pipetting with PBS to remove unbound peptide and transferred to sterile 24 well plates to be used in experiments.

Antimicrobial Activity on Substrates

Antimicrobial activity of TiBP-Spacer5-AMP biocoated titanium surfaces against each bacterial strain was evaluated by culturing bacteria in 24 well plates containing bio-coated surfaces or bare, untreated control surfaces. Bacteria grown to mid-log phase at a concentration of 107 CFU/mL were harvested by centrifugation at 2000×g for 5 min followed by resuspension in 500 µL of appropriate media, transferred to sterile 2 mL centrifuge tubes, and then centrifuged at 2000×g for three minutes.[24] The supernatant was carefully removed from the pellet and the pellet resuspended in PBS at final concentration of 108 CFU/mL and 500 µL of suspension was added to wells containing foil surfaces and 1000 µL to wells with implants. Well plates with TiBP-Spacer5-AMP biocoated surfaces were incubated for two hours at 37° C. in the presence of 5% $CO_2$-supplemented atmosphere for S. mutans and in aerobic atmosphere and 200 rpm shaking for S. epidermidis. Following incubation all surfaces were washed with PBS to remove unbound bacteria. Bacteria were fixed with 1 mL of 2% glutaraldehyde solution for 30 min and then dehydrated in 50%, 70%, 90% and 100% ethanol baths, 10 min for each ethanol concentration. Bacteria were stained with SYTO 9 green fluorescent dye (Life Technologies L7012, Carlsbad, Calif.), incubated for 15 min at room temperature protected from light and excess dye was removed by washing twice with PBS. Stained bacteria were imaged with a fluorescence microscope (Olympus Spin Disk Epifluorescent microscope, Richmond Hill, Ontario, Canada) at an excitation/emission wave number provided by the manufacturer. Five representative fluorescence images were taken for each sample (n=3) and the bacteria were quantified using ImageJ Software and then subjected to statistical analysis.

Host Cell Response

Host cell response was evaluated with a fibroblast cell line (NIH/3T3 ATCC CRL-1658). The fibroblast cells were cultured following the ATCC protocol. Briefly, cells were grown in DMEM media (Gibco 11995073, Carlsbad, Calif.) supplemented with 10% fetal bovine serum (Gibco 10437036) and 1% penicillin-streptomycin (Gibco 15070063) and incubated at 37° C. in a 5% CO2 atmosphere. Fibroblasts were passaged using 0.25% TrypsinEDTA (Gibco 25200072) and cells were counted to ensure correct seeding concentrations. Fibroblast cell response to 60 µM TiBP-Spacer5AMP bio-coating, 200 µg/mL collagen (Sigma C7661, St. Louis, Mo.) coating (positive control) and bare, untreated (negative control) titanium foil and implant surfaces was studied. Fibroblast cells at a concentration of 8×10[5] cells/mL were added to sterile 24 well plates containing TiBP-Spacer5-AMP coated, collagen coated, or bare, untreated foils or implants and incubated for 24 h at 37° C. in a 5% $CO_2$ atmosphere. Fibroblast attachment and spreading were evaluated by fixing fibroblasts on titanium surfaces with 2% glutaraldehyde solution, followed by dehydration in 10%, 30%, 60%, 90% and 100% ethanol. Fixed fibroblasts on titanium surfaces were washed twice with PBS, permeabilized with TritonX (Sigma T8787), sealed with BSA (Fisher BioReagents BP671-10, Carlsbad, Calif.), and stained with Alexa Fluor488-Phalloidin dye (Invitrogen). Unbound dye was removed by washing with PBS and substrates were imaged with a fluorescent microscope at 4, 10 and 20 times magnification. Five representative images of each surface (n=3) were obtained and analyzed with ImageJ Software and then subjected to statistical analysis. Cell attachment was determined as number of cells per square millimeter and the percentage of the image surface covered by attached cells. Another measure of viability, metabolic activity was determined using a MTT (3-(4,5-dimethylthiazol-2-yl)-25-diphenyltetrazolium bromide) assay (Sigma M5655). Following incubation of fibroblasts with TiBP-Spacer5-AMP, collagen, or bare, untreated titanium surfaces for 24 h at 37° C. in a 5% $CO_2$ atmosphere, one tenth of the well liquid volume was removed and replaced by the same volume of 5 mg/mL MTT reagent. The substrates with MTT reagent were incubated for 3 h then transferred to a sterile 24 well plate. The formazan crystals were dissolved in the detergent reagent according to the manufacture's protocol. Absorbance was measured at 570 nm.

Results and Discussion

A chimeric peptide composed of a titanium binding and an antimicrobial domain linked by a novel spacer design (TiBP-Spacer5-AMP) was assessed. The spacer was designed to preserve the secondary structural features of both the TiBP and the AMP so as to impart an effective antimicrobial activity against two bacteria commonly associated with nosocomial implant infections, S. mutans and S. epidermidis.[40,41] Data from a comparative chimeric peptide with identical functional domains, but a shorter spacer sequence (TiBP-Spacer3-AMP) and the AMP peptide alone were used to evaluate the effect of the new engineered spacer design.[24-26] Table 1 contains the sequences and physical chemical properties for each chimeric peptide and their functional domains. Despite the physical and chemical similarity to one another, the functional activity of the two chimeric peptides was quite different. We observed improved antimicrobial activity with the altered amino acid composition designed into the longer spacer called Spacer5.

The interfacial activity model suggests that antimicrobial activity depends on amino acid composition and physical chemical properties.[42] Interfacial activity encompasses the electrostatic and hydrophobic interactions between peptides and the lipid surface of the bacterial cell wall. Literature suggests several mechanisms leading to cell death following interaction between the peptide and the lipid surface including a compromised bacterial cell wall which initiates a cascade of effects including cellular respiration, DNA damage and altered gene expression. Recent publications indicate the production of reactive oxygen species (ROS) when AMPs attack bacteria.[43-45] Much of the literature characterize AMP activity based on either structure-function relationships or physical chemical properties.[42] The effect of the engineered spacer design was evaluated through independent, but corroborating approaches, including: measurement of antimicrobial activity of the chimeric peptide in solution, as well as when bound to titanium substrates against common nosocomial microorganisms allowing us to suggest that the restored antimicrobial activity is due to the preserved structure associated with the Spacer5 design.

TABLE 1

Physical chemical properties and amino acid sequences for titanium binding peptide (TiBP), antimicrobial peptide (AMP), and two chimeric peptides TiBP-Spacer3-AMP and TiBP-Spacer5-AMP.

| Name | Sequence | Spacer Length | MW (kDa) | pI | Charge | GRAVY |
|---|---|---|---|---|---|---|
| TiBP | RPRENRGRERGL (SEQ ID NO: 7) | N/A | 1.4956 | 11.82 | +3 | −2.633 |
| AMP | LKLLKKLLKLLKKL (SEQ ID NO: 8) | N/A | 1.6923 | 10.70 | +6 | 0.500 |
| TiBP-Spacer3-AMP | RPRENRGRERGL-GGG-LKLLKKLLKLLKKL (SEQ ID NO: 9) | 3 | 3.3411 | 11.85 | +9 | −0.890 |
| TiBP-Spacer5-AMP | RPRENRGRERGL-GSGGG-LKLLKKLLKLLKKL (SEQ ID NO: 10) | 5 | 3.4852 | 11.85 | +9 | −0.871 |

Abbreviations:
MW, molecular weight;
pI, isoelectric point; and
GRAVY, GRand Average Value of hydropathicitY.
Despite chimeric peptide similarity to one another, we observed improved antimicrobial activity with the altered amino acid composition of the longer peptide spacer, Spacer5.

Computational Structure Predictions

Figure 9:
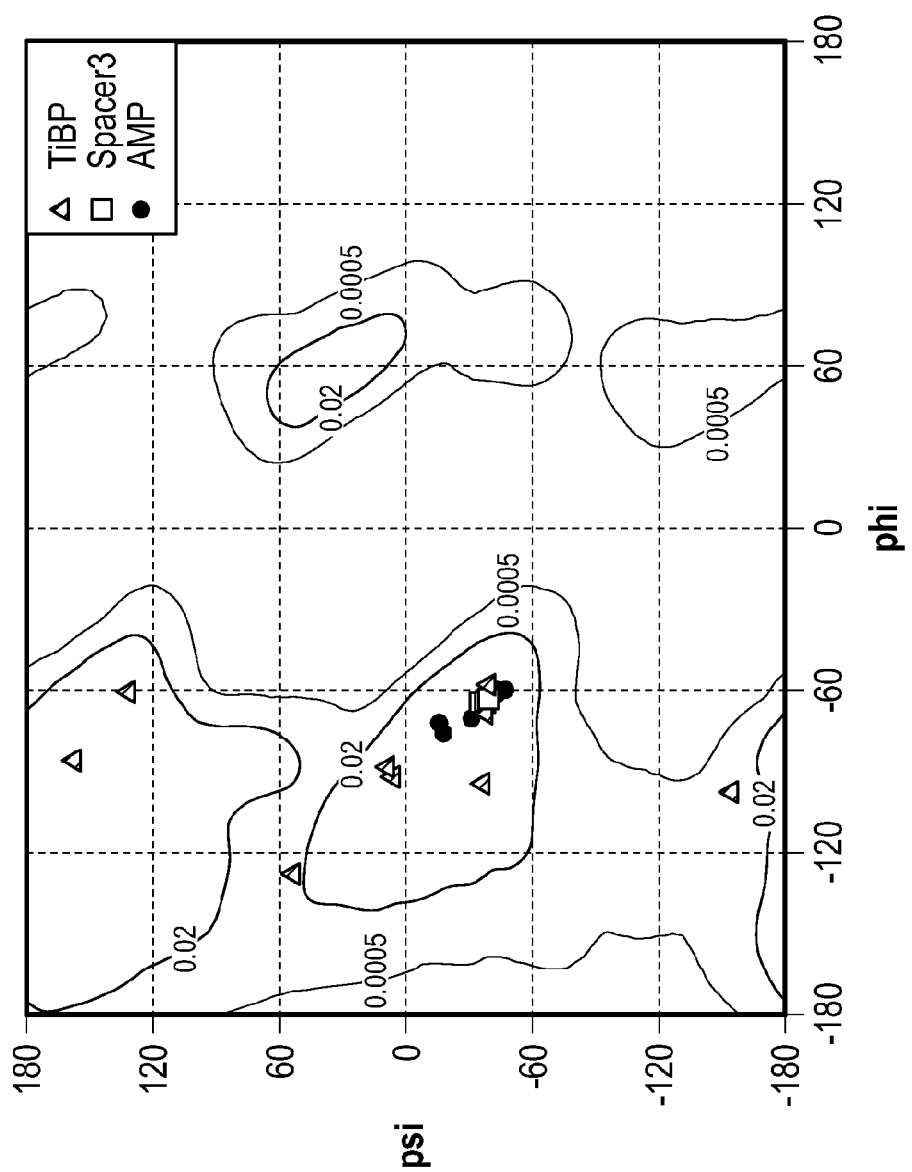
FIG. 9 provides a Ramachandran Plot of TiBP-Spacer3-AMP generated from the lowest energy computationally generated structure. Orange triangles, green squares, and blue circles, designate contributions from TiBP, Spacer3, and AMP domains, respectively. Psi/phi angles (−90°, −60°) predicting prominent alpha helix structure involving most amino acid residues in TiBP-Spacer3-AMP chimeric peptide.
Figure 10:
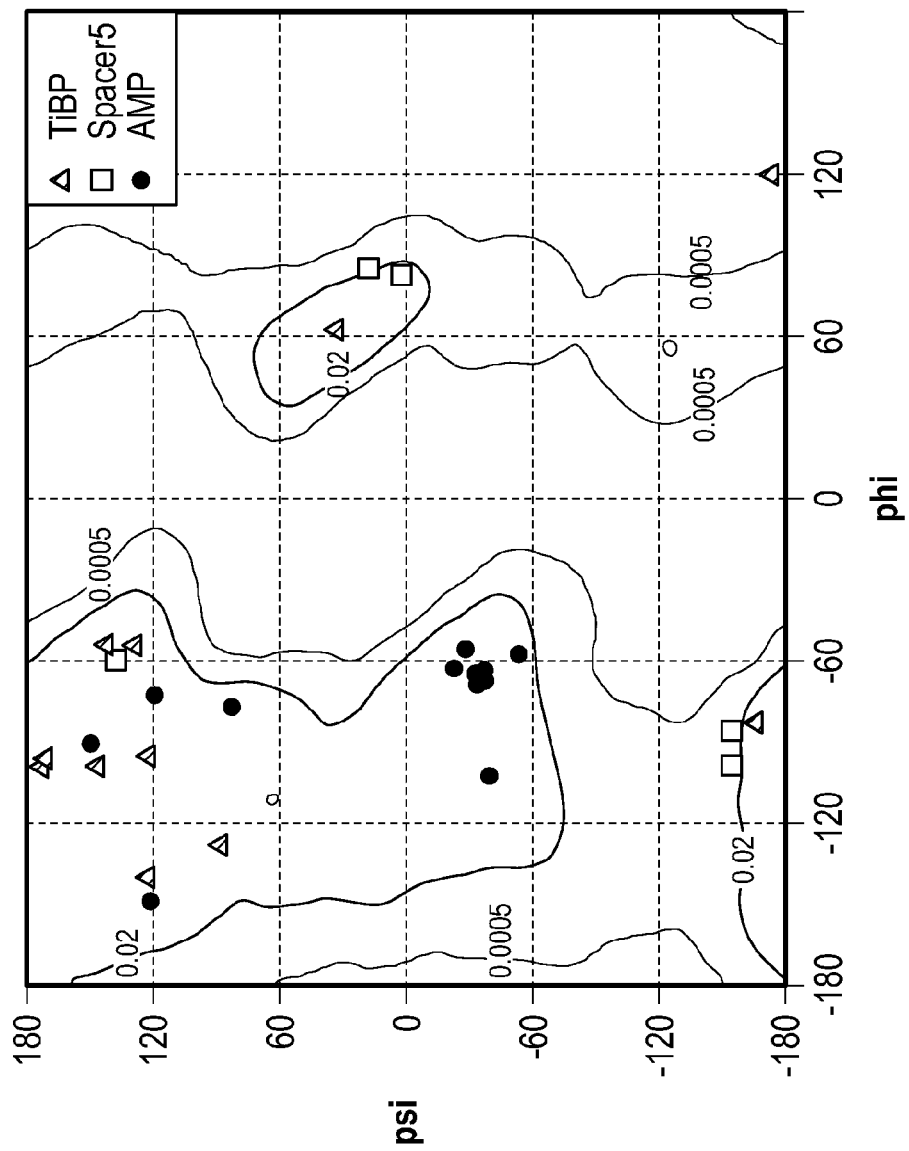
FIG. 10 provides a Ramachandran Plot of TiBP-Spacer5-AMP generated from the lowest energy computationally generated structure. Orange triangles, green squares, and blue circles, designate contributions from TiBP, Spacer5, and AMP domains, respectively. Psi/phi angles (−90°, −60°) corresponding to alpha helicity are assigned to the AMP domain, while psi/phi angles (−90°, +120°) corresponding to beta sheet/random coil secondary structures are observed in the rest of the molecule.

Computational molecular structures were generated using the PyRosetta structural ensemble generation method.[33] One thousand likely energy minimized structures were generated for each chimeric peptide, for each spacer sequence, and for each functional domain. The lowest energy structure for each is depicted in FIG. 1 with TiBP, spacer domain, and AMP designated with blue-, black-, and red-shading, respectively. The images shown in FIG. 1 represent likely structures that are modeled in solution. Ramachandran plots were generated for the lowest energy chimeric peptide structures and are shown as FIGS. 9 and 10 for TiBP-Spacer3-AMP and TiBP-Spacer5-AMP, respectively. The Ramachandran plots simulates the contribution of hydrogen bonding among backbone atoms and can be interpreted to correlate the contribution of the α-helix or β-sheet structural features depicted in the energy minimized structures.

We first examined the structure of the chimeric peptides.[24] The computational structures in FIG. 1 show the secondary structure features for the chimeric peptides and their component parts. The structure of both TiBP and AMP peptides show features of alpha helicity with a stronger helicity prominence in the AMP domain (FIG. 1E). TiBP-Spacer3-AMP (FIG. 1A) has an α-helix feature beginning within the AMP domain and preserved through Spacer3. From the Ramachandran plot we conclude the α-helix feature is approximately 26 amino acids long and confirm that backbone angles consistent with α-helix features are present though AMP, Spacer3, and almost the entire TiBP. All but three amino acids correspond to psi/phi angles (−90°, −60°) consistent with α-helix. Spacer3 consists of but three glycine amino acid residues; therefore the minimal side chain size of glycine in Spacer3 could allow the alpha helix feature to be preserved across the spacer domain and into the TiBP, producing longer alpha helices. The alpha helix feature in TiBP-Spacer5-AMP is comparatively much shorter. The Ramachandran plot for TiBP-Spacer5-AMP shows the psi/phi angles (−90°, −60°) corresponding to alpha helicity are assigned to the AMP domain, while psi/phi angles (−90°, +120°) corresponding to β-sheet/random coil secondary structures are observed in the rest of the molecule. Without wishing to be bound to any particular theory, we interpret these findings to suggest that the Spacer5 segregates the AMP domain from the rest of the chimeric peptide, allowing its antimicrobial activity to be preserved.

The Spacer5 (GSGGG) (SEQ ID NO: 2) is composed of four glycine amino acid residues and a single serine amino acid residue. The presence of a polar serine residue could produce a slight "ST staple" feature in the spacer region producing a backbone bend that prevents the continuity of the alpha helix feature observed in TiBP-Spacer3-AMP. Table 2 shows the percentage of α-helix frequency over either a four or five amino acid average for the two chimeric peptides. Of the 1000 structures generated in the ensembles for each chimeric peptide, TiBP-Spacer5-AMP had a larger percentage of structural topologies represented with four or five amino acid residue alpha helix features. This is consistent with what we observed with the detailed structure analysis conducted for the lowest energy structure of each chimeric peptide. We next turned to CD analysis which can directly measure secondary structure of TiBP-Spacer5-AMP.

TABLE 2

Percent of helix frequency over either a four or five amino acid average.

| Peptide | 4-aa Alpha Helix Frequency (%) | 5-aa Alpha Helix Frequency (%) |
|---|---|---|
| TiBP-Spacer3-AMP | 10.4 | 5.6 |
| TiBP-Spacer5-AMP | 17.6 | 8.0 |

Structure Determination with CD

Figure 2:
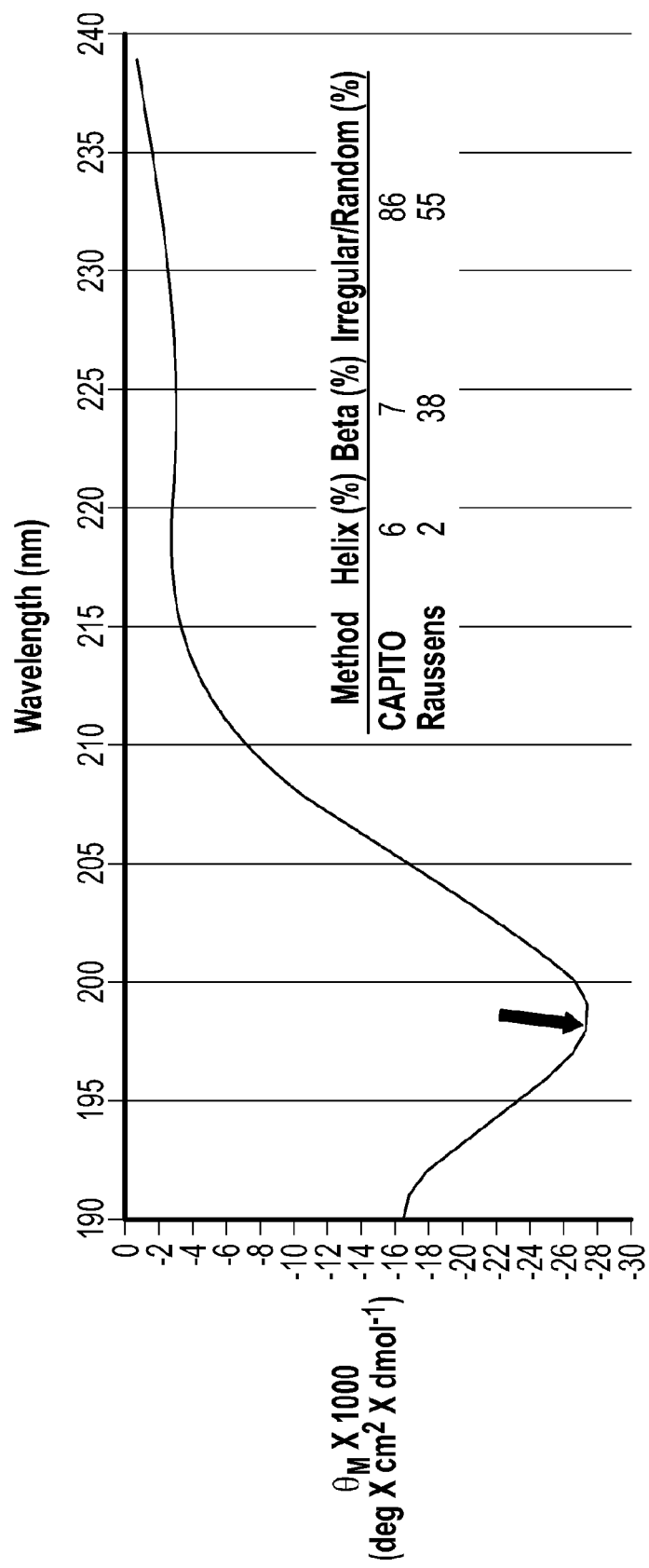
FIG. 2 provides a circular dichroism (CD) spectrum for TiBP-Spacer5-AMP chimeric peptide at a concentration of 50 µM in phosphate buffered saline, pH 7.4. The feature designated by the arrow indicates a greater preference for right-circularly polarized light absorbance compared to the spectrum for chimeric peptide with Spacer3.[1][6] The CAPITO and Raussens methods indicates a predominance of irregular and random coil features in the spectrum consistent with what is observed in the computationally generated secondary structure for TiBP-Spacer5-AMP shown in FIG. 1B.[38,39]

The chimeric peptide was prepared at a concentration of 50 μM in PBS at pH of 7.4 for secondary structure analysis by CD. Two complementary methods, the CAPITO and the Raussens method were used to quantify the results obtained from the CD spectra.[38,39] We applied both the concentration dependent CAPITO method and the concentration independent Raussens method for these predictions to corroborate outcomes. Both approaches are regression methods used to transform CD spectral data in order to identify corresponding structural information from a protein database. The CD spectrum for TiBP-Spacer5-AMP is depicted in FIG. 2 with inset table containing results from analysis with the regression methods. The spectrum for the chimeric peptide with Spacer5 indicates a greater preference for right-circularly polarized light absorbance compared to the previously published spectrum for Spacer3, indicating that the predominance of α-helix secondary structure present in TiBP-Spacer3-AMP is not preserved through the newly designed Spacer5.[26] The CD structural prediction results are consistent with the computationally predicted secondary structure analysis, indicating that a majority of the secondary structure of TiBP-Spacer5-AMP is β-sheet or random coil. Moreover, both the CAPITO and Raussens method assign 86% and 55% secondary structure to irregular or random coil features, for TiBP-Spacer5-AMP, respectively. In addition to random coil features, the Raussens method assigns 38% of TiBP-Spacer5-AMP secondary structure to beta sheet features. The Raussens method also corroborates the Ramachandran plot prediction for analysis computationally generated structures.

Chimeric Peptide Function

Antimicrobial Effect in Solution

Antimicrobial activity in solution was elucidated by determining the MIC of TiBP-Spacer5-AMP required to inhibit growth for two bacterial strains commonly recovered from infected implants, S. mutans and S. epidermidis.[40,41] Previously published MIC values for TiBP-Spacer3-AMP and AMP alone were used for comparison.[24] MIC data for AMP, TiBP-Spacer3-AMP, and TiBP-Spacer5-AMP are depicted in Table 3. The MIC value of TiBP-Spacer5-AMP against S. mutans and S. epidermidis are 50 μM and 8 μM, respectively. We observed a remarkable three-fold improvement of MIC antimicrobial activity for the TiBP-Spacer5-AMP against S. mutans. This can be attributed to the increased frequency of secondary structural features corresponding to antimicrobial activity as predicted by the "rule induction method", corroborating the importance of secondary structure features in AMP design. Without wishing to be bound to any particular theory, the design of the spacer offers an opportunity to fine-tune the structural properties of the chimeric peptide so as to improve its antimicrobial potential. The use of the Spacer5 results in a chimeric peptide displaying shorter α-helix structural features compared to Spacer3 and yields improved antimicrobial activity.

The bactericidal concentration for TiBP-Spacer5-AMP against each bacteria was also determined using the AlamarBlue assay.[46] The bactericidal concentration for TiBP-Spacer5-AMP was found to be 60 μM for S. mutans and 10 μM for S. epidermidis. These concentrations are only slightly higher than the observed MIC values indicating that TiBP-Spacer5-AMP corroborating these complementary methods of killing bacteria. Next, we used the bactericidal concentrations determined from the AlamarBlue assay to assess the antimicrobial activity of medical implants coated with TiBP-Spacer5-AMP by assessing bacterial growth on their surfaces.

TABLE 3

Minimum Inhibitory Concentration (MIC) of TiBP-Spacer5-AMP, TiBP-Spacer3-AMP, and AMP alone in solution against S. mutans and S. epidermidis. There is a three-fold decrease in TiBP-Spacer5-AMP MIC against S. mutans.

| Peptide | S. mutans (μM) | S. epidermidis (μM) |
|---|---|---|
| AMP | 38 | 4 |
| TiBP-Spacer3-AMP | 153 | 5 |
| TiBP-Spacer5-AMP | 50 | 8 |

Antimicrobial Effect on Surfaces

Figure 3A:
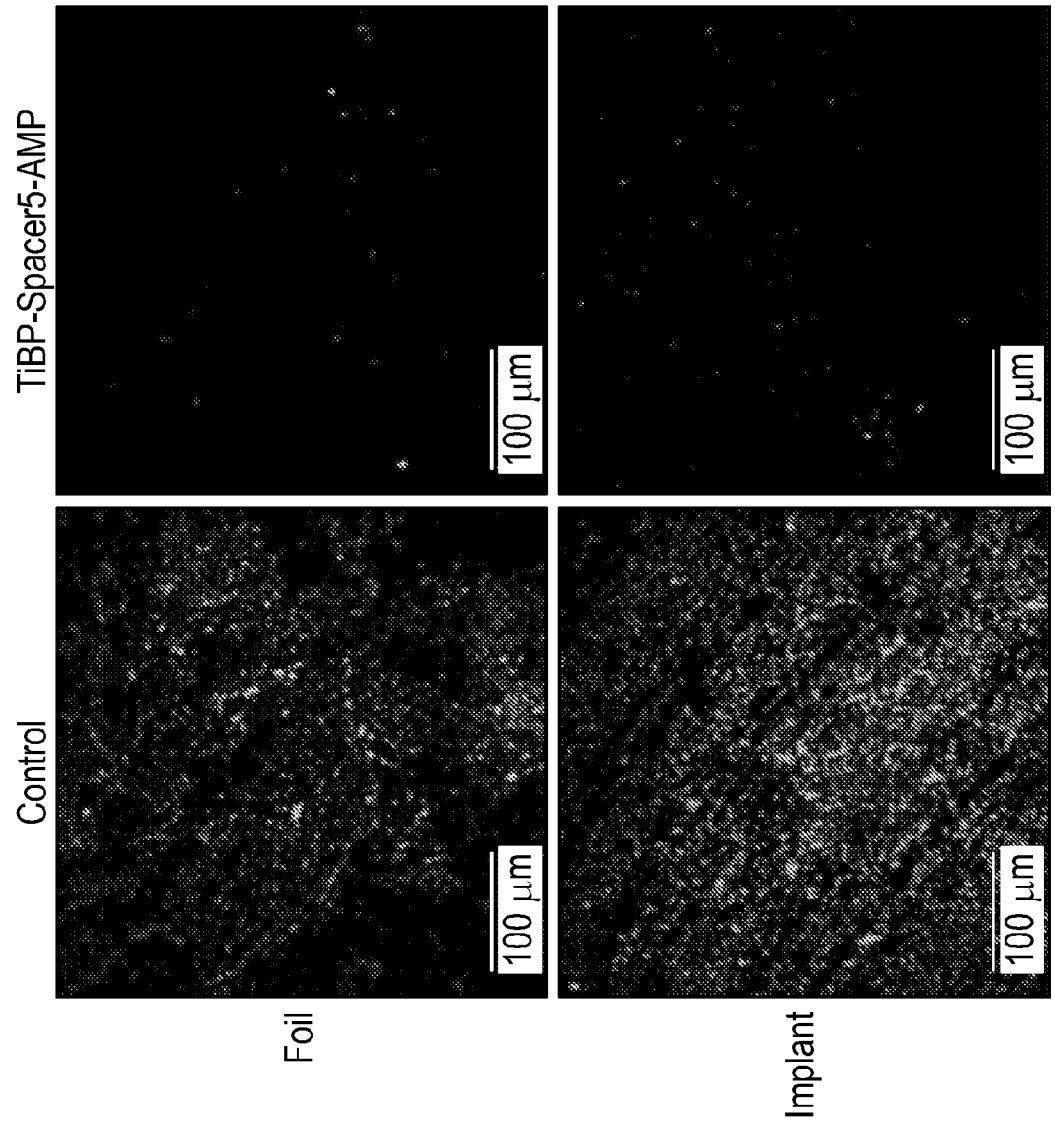
FIG. 3 provides fluorescent microscope images (Scale Bar is 100 µm) of S. mutans bacteria on 99% pure titanium foils and orthopedic implant discs with TiBP-Spacer5-AMP biocoating and bare, bare untreated controls (FIG. 3A) as well as a chart depicting the percent surface coverage quantified by ImageJ of bacteria on the titanium surfaces (FIG. 3B).
Figure 3B:
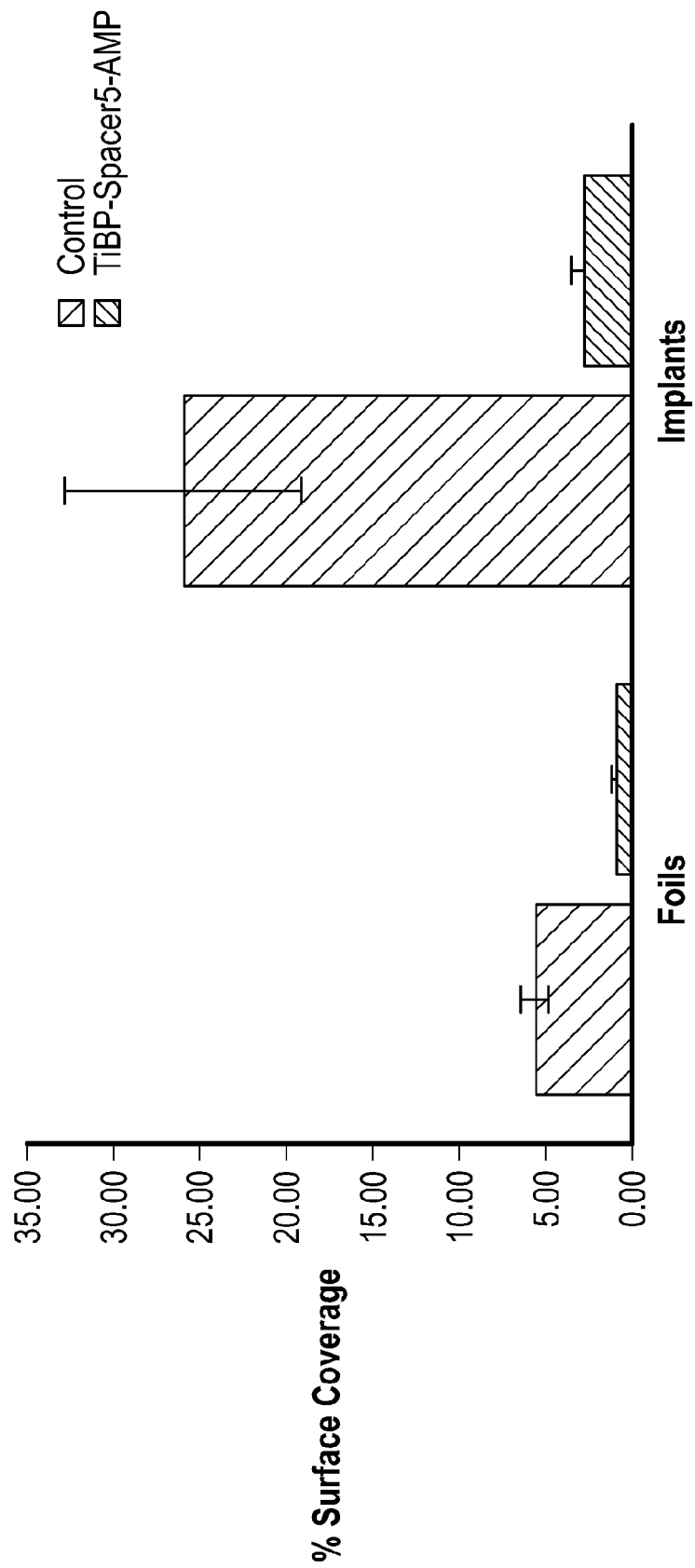
Figure 4A:
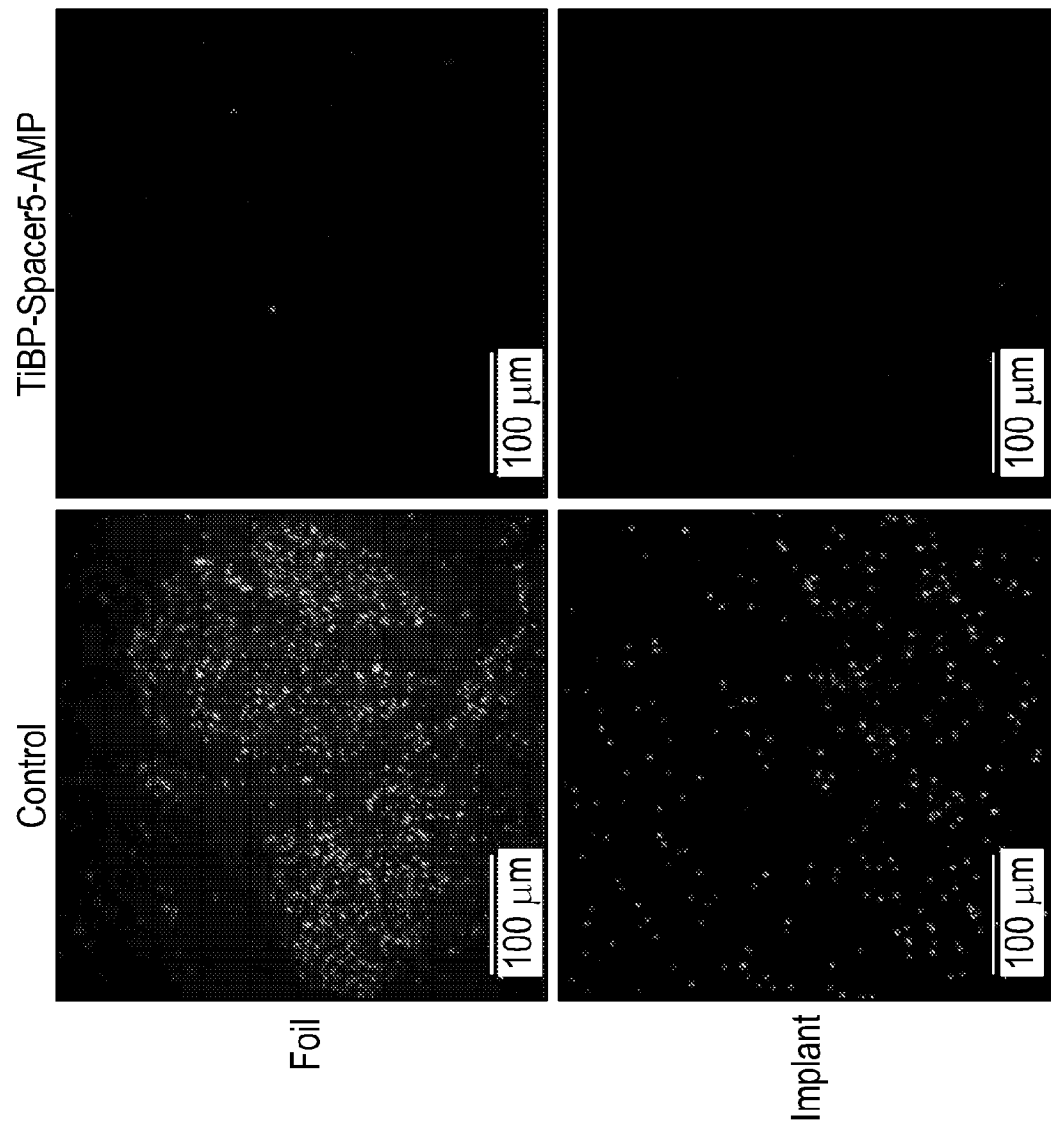
FIG. 4 provides fluorescent microscope images (Scale Bar is 100 µm) of S. epidermidis bacteria on 99% pure titanium foils and orthopedic implant discs with TiBP-Spacer5-AMP bio-coating and bare, bare untreated controls (FIG. 4A) as well as a chart depicting the percent surface coverage quantified by ImageJ of bacteria on the titanium surfaces (FIG. 4B).
Figure 4B:
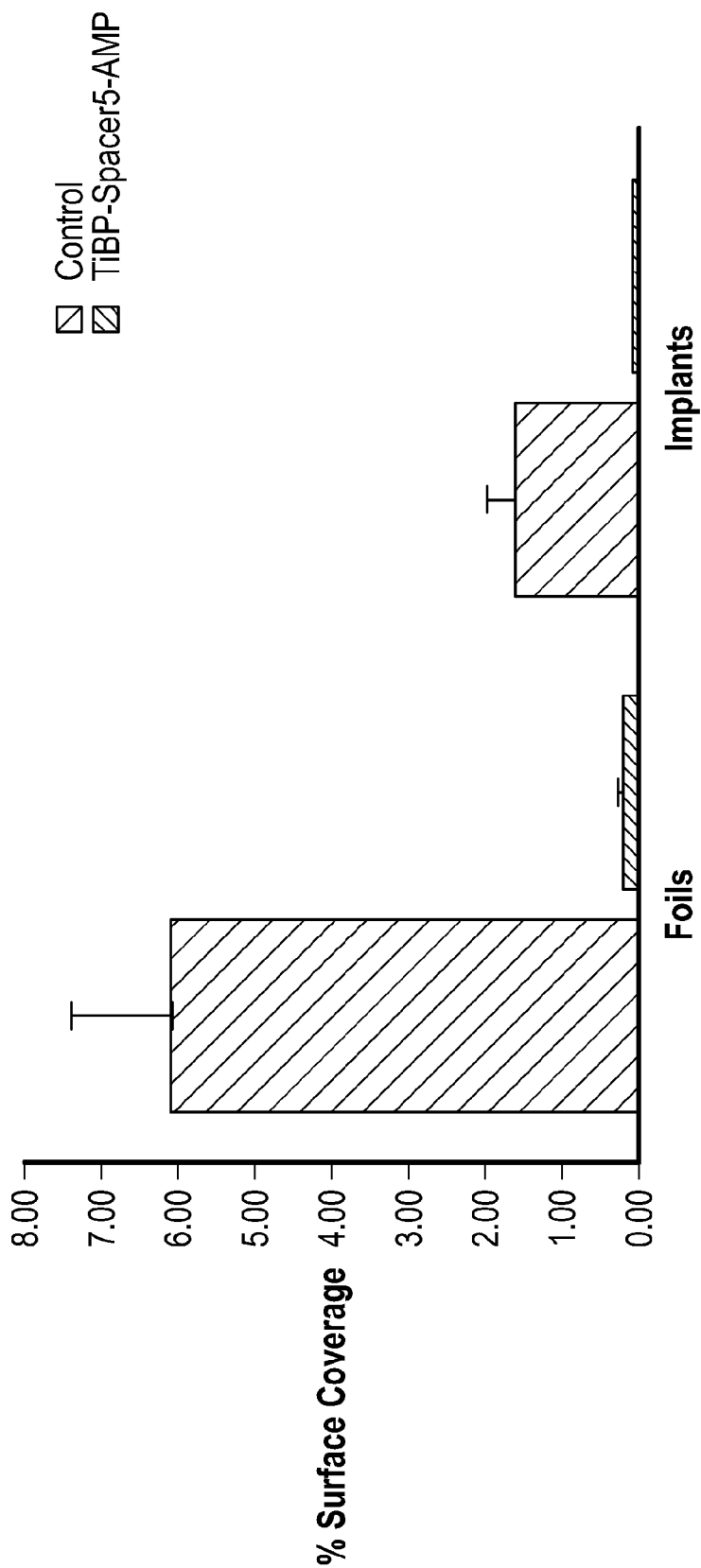

TiBP-Spacer5-AMP at 60 μM for S. mutans and 10 μM for S. epidermidis were permitted to self-assemble on selected titanium surfaces and evaluated for their antimicrobial activity. Titanium foils were selected for their ease of use, while discs cut from stock titanium orthopedic bar material were used to ascertain their effectiveness directly on a clinically relevant surface. For both surfaces, infectious organisms common to clinical infections, S. mutans and S. epidermidis, were used to evaluate the antimicrobial activity of the bio-coating. Previous studies had established the binding characteristics and affinity for the TiBP as part of a chimeric molecule.[24] Following incubation, the unbound peptide was removed by repeated washing, suggesting the antimicrobial activity observed for either titanium surface was the result of the chimeric peptide bound to the surface representing antimicrobial activity. The observed effectiveness of TiBP-Spacer5-AMP antimicrobial effect against S. mutans is shown in FIG. 3 and against S. epidermidis in FIG. 4. The images are representative areas, and the percent of the total surface area covered by bound bacteria was identified by bacterial staining and quantified by analysis with ImageJ. In all cases, TiBP-Spacer5-AMP bio-coating reduced the number of bacteria attached to the surface compared to uncoated control surfaces. The fold reduction for the number of bacteria on titanium surfaces with TiBP-Spacer5-AMP bio-coating is depicted in Table 4. There is a six-nine-fold reduction for S. mutans, with a 33-48-fold improvement noted for S. epidermidis on foil or implant surfaces, respectively, due to the presence of the TiBP-Spacer5-AMP bio-coating. These data suggest that the TiBP-Spacer5-AMP bio-coating is an effective strategy to combat infections and consequential implant failure by reducing bacterial colonization which ultimately transform to a complex biofilm that can resist systemic administration of antibiotics and lead to implant failure.[47] Alternatively, the coating formed by the TiBP-Spacer5-AMP may interfere with bacterial attachment by forming a biomimetic surface that is less fouling than the bare titanium or titanium alloy surface.[31] The increasing frequency of antibiotic resistant bacteria in hospital settings contributing to nosocomial infections and the increasing number of patients with co-morbidities can both contribute to a diminished ability of the host to resist and clear bacteria at surgical sites which lead to implant failure. Whether by antimicrobial activity or reduced attachment, the reduction in the number of pathogenic bacterial by the TiBP-Spacer5-AMP would result in improved patient outcomes. Lastly, we evaluated host cell response on titanium surfaces coated with the TiBP-Spacer5-AMP chimeric peptide.

TABLE 4

Fold improvement calculated from fluorescent microscopy image analysis of S. mutans and S. epidermidis bacteria on titanium foil and implant surfaces with TiBP-Spacer5-AMP bio-coating, compared to bare, uncoated control surfaces. There is in resistance to bacteria as a result of the TiBP-Spacer5-AMP bio-coating on foil and implant surfaces.

| Fold Improvement Compared to Uncoated Ti Surfaces | | |
|---|---|---|
| | Foils | Implants |
| TiBP-Spacer5-AMP against S. mutans | 6 | 9 |
| TiBP-Spacer5-AMP against S. epidermidis | 33 | 48 |

Host Cell Attachment and Viability

Figure 5:
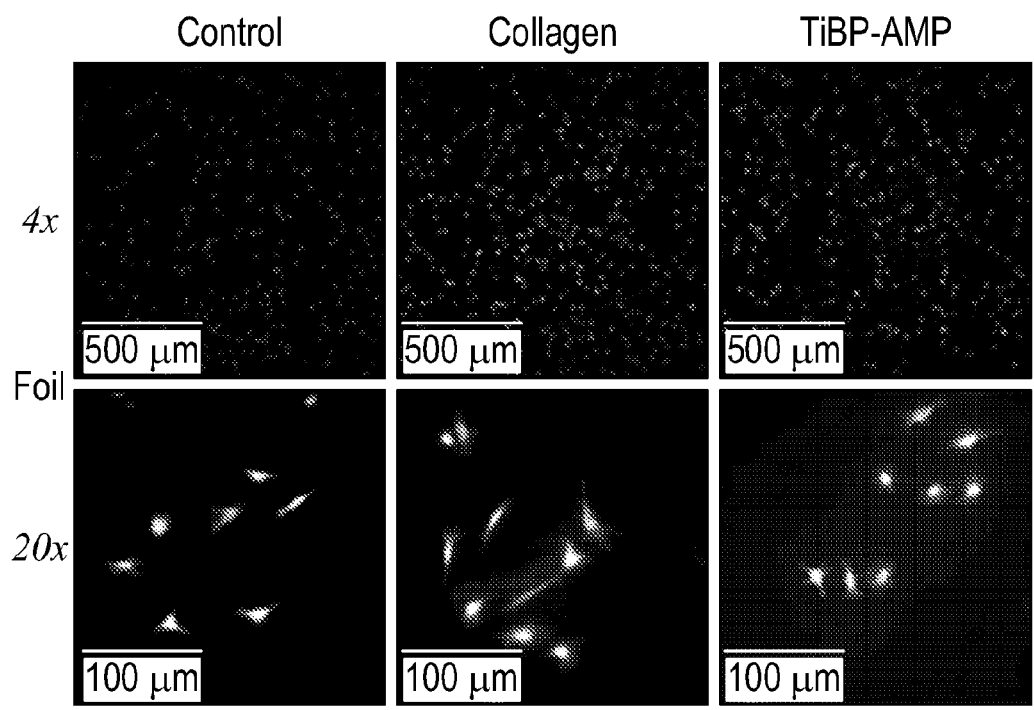
FIG. 5 provides fluorescent images of NIH/3T3 fibroblast attachment on titanium foils: Control (no treatment), Collagen (200 µg/mL collagen coating positive control), or TiBP-AMP (60 µM TiBP-Spacer5-AMP bio-coating). Scale bar represents 500 µm for 4× images and 100 µm for 20× images. TiBP-Spacer5-AMP bio-coated foils had fewer fibroblasts attach compared to untreated control, however the fibroblast surface coverage for TiBP-Spacer5-AMP was greater indicating the cells spread more.
Figure 5:
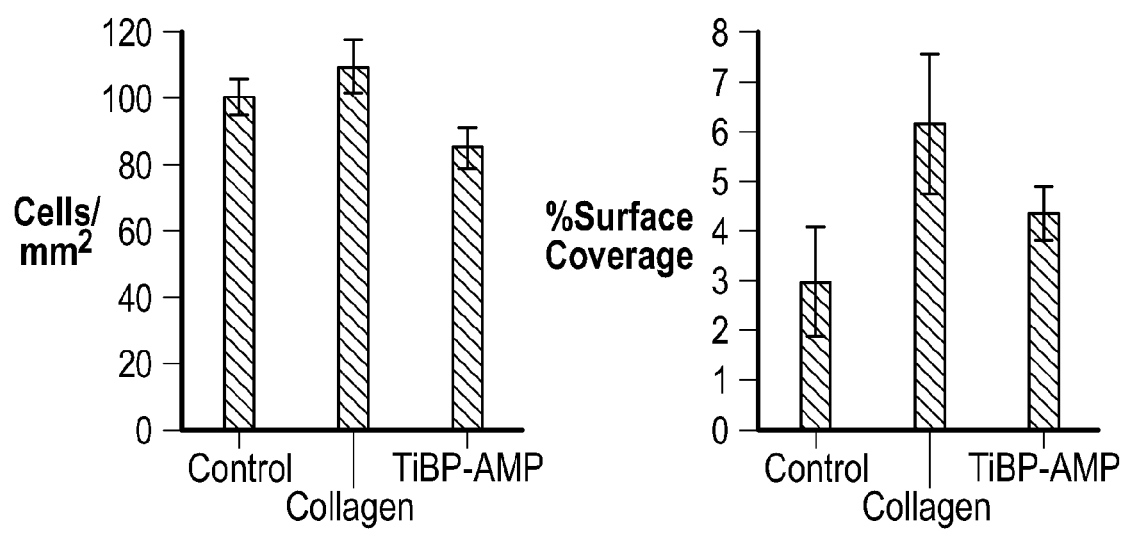
Figure 6:
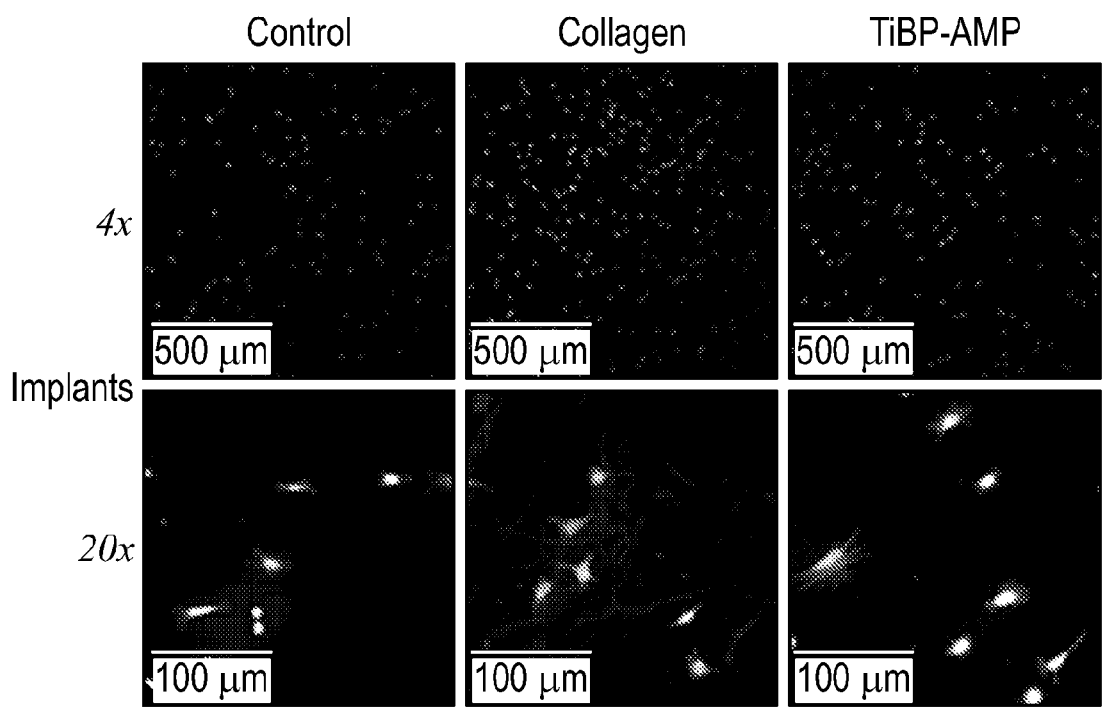
FIG. 6 provides fluorescent images of NIH/3T3 fibroblast attachment on titanium orthopedic implants: Control (no treatment), Collagen (200 µg/mL collagen coating positive control), or TiBP-AMP (60 µM TiBP-Spacer5-AMP bio-coating). Scale bar represents 500 µm for 4× images and 100 µm for 20× images. TiBP-Spacer5-AMP bio-coated implants showed greater cell attachment and spreading compared to untreated controls and attachment and spreading were comparable to collagen positive controls.
Figure 6:
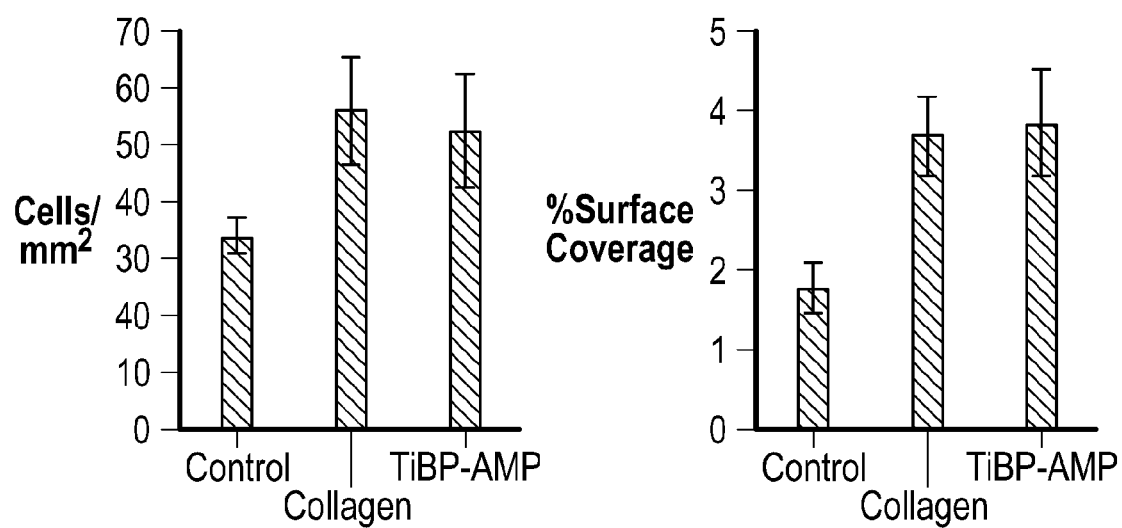

Host cell attachment and viability was evaluated in vitro using a fibroblast cell line (NIH/3T3) by measuring cell attachment, morphology/spreading, and viability response to TiBP-Spacer5-AMP coated substrates. The results are shown in FIG. 5 for titanium foils and those for orthopedic implants are shown in FIG. 6. The number of fibroblasts that attached to the TiBP-Spacer5-AMP bio-coated foils was not statistically different compared to an untreated control surface. However, the cells attached on the chimeric peptide bio-coated foil surface did demonstrate greater coverage, suggesting they spread more effectively compared to cells grown on untreated control surfaces. As expected, collagen-coated surfaces, the gold-standard used as a positive control, did outperform the TiBP-Spacer5-AMP chimeric peptide bio-coating. Interestingly, for studies with fibroblasts seeded onto titanium implant surfaces, the chimeric peptide bio-coated surfaces showed statistically greater cell attachment and spreading properties than observed for the unmodified implant substrates. Additionally, the TiBP-Spacer5-AMP bio-coated implant surfaces showed adhesion and spreading results that were statistically comparable to the positive collagen controls. These results suggest that bio-coating orthopedic medical implants with TiBP-Spacer5-AMP would result in an improved host cell response at the implant tissue interface.

Figure 7:
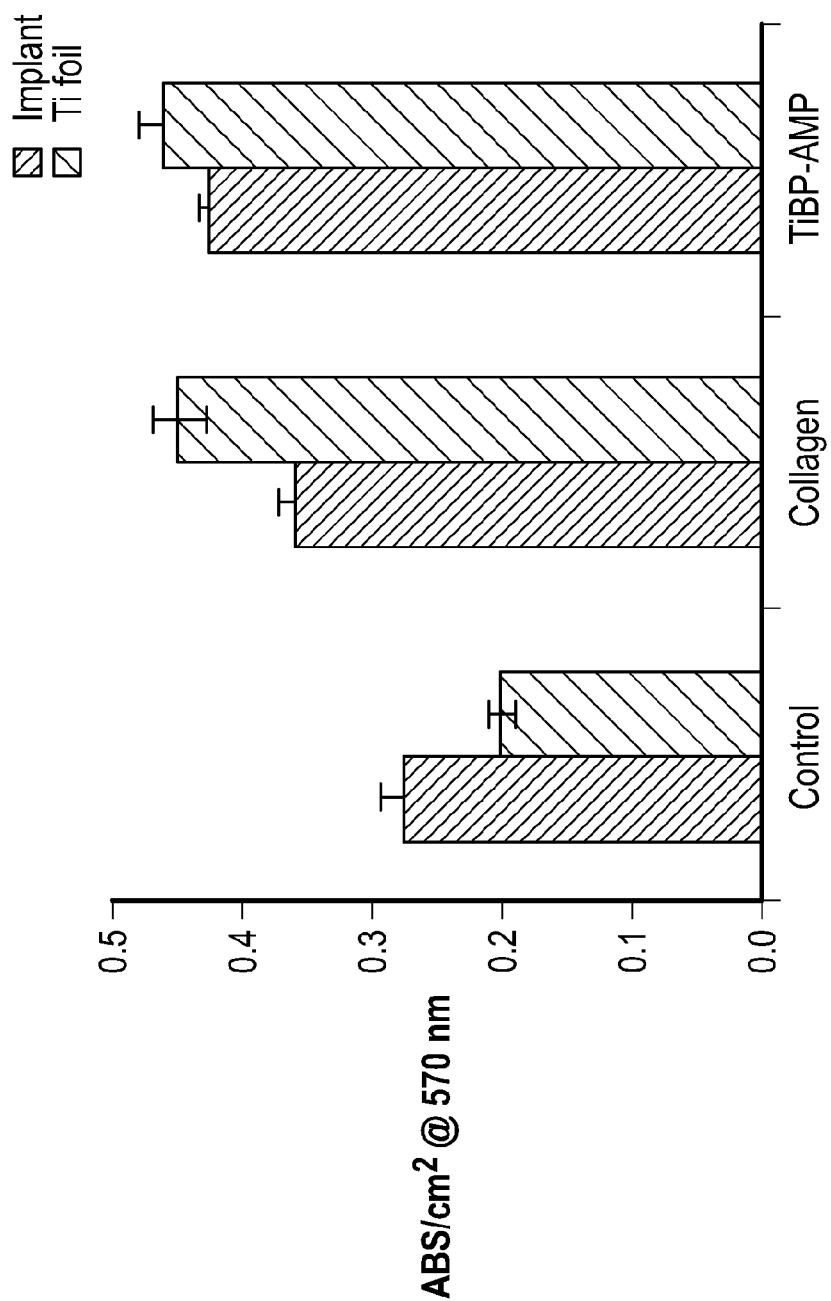
FIG. 7 provides NIH/3T3 fibroblast metabolism on titanium foils and implants measured by MTT assay. Control (no treatment), collagen (coated with 200 µg/mL collagen), TiBP-AMP (coated with TiBP-Spacer5-AMP at 60 µM).
Figure 8:
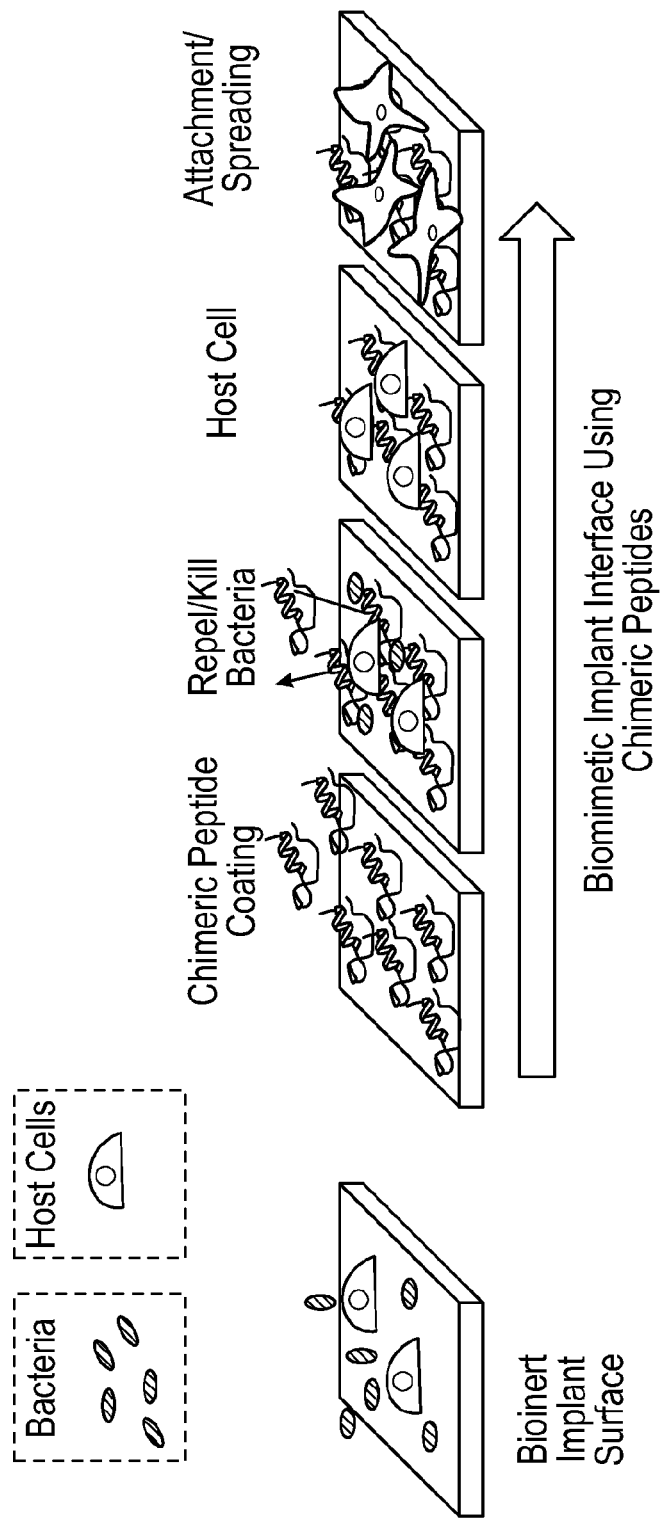
FIG. 8 is a schematic illustration of a surface of an implant coated with a chimeric peptide according to an illustrative embodiment demonstrating its antimicrobial behavior without negatively affecting host cell attachment and viability.

The MTT assay was used as a live-dead discrimination assay for fibroblasts grown on various surfaces. We found that cell viability on either titanium foils or implant surfaces treated with chimeric peptide were similar to values observed for the positive control collagen coated surfaces (FIG. 7), with approximately 50% greater cell viability observed compared to untreated surfaces.

Conclusion

A titanium binding, antimicrobial chimeric peptide with novel spacer design (TiBP-Spacer5-AMP) was rationally engineered. Computational structure analysis revealed secondary structural features that were dependent on the length and composition of the spacer. These features were confirmed through direct evaluation with CD. Specifically, TiBP-Spacer5-AMP has multiple short α-helix features with predominately irregular or random coil secondary structure corroborated by Ramachandran plot analysis of energy minimized structures and CD. In fact, a three-fold decrease in MIC that indicates increased antimicrobial activity was observed against bacteria common to nosocomial implant infection. TiBP-Spacer5-AMP was assembled on titanium foils and orthopedic implant surfaces as a biomimetic coating which reduced bacterial numbers nine-fold against *S. mutans*, a bacteria common to dental implant infections, and 48-fold against *S. epidermidis* bacteria common to orthopedic implant infections. The potential of the chimeric peptide biocoating to promote host cell attachment was evaluated using a fibroblast cell line. On chimeric peptide bio-coated surfaces, the cells attached, spread and exhibited 50% greater viability measured by a metabolic assay compared to identical cells on bare, untreated titanium surfaces. Data from the TiBP-Spacer5-AMP point to the importance of optimal design of the spacer between two functional domains within the chimeric peptide in order to optimize the function of each domain, namely binding and self-assembling onto titanium surfaces and the displayed antimicrobial activity on the biomaterial surface. The ability to create an antimicrobial bio-coating on titanium medical implants that serve to overcome complications associated with implant failure due to nascent infection and their eventual loss by infection that contributes to increasing medical costs and patient morbidity has interminable value.

TABLE 5

Concentrations of TiBP-Spacer5-AMP evaluated against S. mutans and S. epidermidis in solution. Growth was monitored every two hours for 24 hours by measuring the optical density at 600 nm ($OD_{600}$) corresponding to bacterial CFU/mL. Entries with a "+" indicate bacterial growth did occur at that concentration of TiBP-Spacer5-AMP, whereas entries with a "−" indicate inhibition of bacterial growth. The MIC of TiBP-Spacer5-AMP against S. mutans and S. epidermidis is 50 μM and 8 μM, respectively.

| S. mutans | | | | | | | | | |
|---|---|---|---|---|---|---|---|---|---|
| TiBP-Spacer5-AMP | 0 μM | 5 μM | 10 μM | 20 μM | 30 μM | 40 μM | 50 μM | 60 μM | 70 μM |
| Growth | | + | + | + | + | + | − | − | − |
| | | | | | | | MIC is 50 μM | | |

| S. epidermidis | | | | | | | | | |
|---|---|---|---|---|---|---|---|---|---|
| TiBP-Spacer5-AMP | 0 μM | 1 μM | 2 μM | 3 μM | 4 μM | 5 μM | 6 μM | 7 μM | 8 μM |
| Growth | | + | + | + | + | + | + | + | − |
| | | | | | | | | MIC is 8 μM | |

Another exemplary titanium binding peptide sequence is TiBP2 (RPREQRGERPRP) (SEQ ID NO: 56). Exemplary titanium binding chimeric peptides include: TiBP-WLM-NYFWPL-AMP1: RPRENRGRERGL-WLMNYFWPL-LKLLKKLLKLLKKL (SEQ ID NO: 57); TiBP-YLM-NYLLPY-AMP1: RPRENRGRERGL-YLMNYLLPY-LKLLKKLLKLLKKL (SEQ ID NO: 58); TiBP-PKSALQEL-AMP1: RPRENRGRERGL-PKSALQEL-LKLLKKLLKLLKKL (SEQ ID NO: 59); TiBP-KGSVLSAD-AMP1: RPRENRGRERGL-KGSVLSAD-LKLLKKLLKLLKK (SEQ ID NO: 60); TiBP2-WLMNYFWPL-AMP1: RPREQRGERPRP-WLMNYFWPL-LKLLKKLLKLLKKL (SEQ ID NO: 61); TiBP2-YLMNYLLPY-AMP1: RPREQRGERPRP-YLM-NYLLPY-LKLLKKLLKLLKKL (SEQ ID NO: 62); TiBP2-PKSALQEL-AMP1: RPREQRGERPRP-PKSALQEL-LKLLKKLLKLLKKL (SEQ ID NO: 63); TiBP2-KGSVLSAD-AMP1: RPREQRGERPRP-KGSVLSAD-LKLLKKLLKLLKK (SEQ ID NO: 64); TiBP2-Spacer3-AMP1: RPREQRGERPRP-GGG-LKLLKKLLKLLKKL (SEQ ID NO: 65); TiBP2-Spacer5-AMP1: RPREQRGER-PRP-GSGGG-LKLLKKLLKLLKKL (SEQ ID NO: 66).

Example 2. Design and Characterization of Novel Antimicrobial Peptides

Antibacterial Screening Test

*S. epidermidis*, a common pathogen for surgical site infections, was used to evaluate antibacterial activity on agar plates. *Staphylococcus epidermidis* ATCC® 29886™ was used in the present study. The strain was cultured according to ATCC® protocol using the following media: Nutrient Broth (NB) (Difco 0003) for *S. epidermidis*. The bacterial pellet obtained from ATCC was rehydrated in 0.5 mL of the above-specified media, and several drops of the suspension were immediately placed and streaked on an agar slant of the specified media. The agar-plate was then incubated aerobically at 37° C. for 24 hours. Overnight cultures of *S. epidermidis* were made by aseptically transferring a single-colony forming unit into 10 mL of NB, followed by aerobic incubation at 37° C. with constant agitation (200 rpm) for 16 hours.

AMP functional peptide candidates were screened for antimicrobial function using a zone of inhibition assay on agar plates. Crude peptides were dissolved in dimethyl sulfoxide (DMSO)/$H_2O$. The bacterial growth culture was spread on agar plates using a sterile cotton swab then 10 μL of the solubilized peptide candidates were pipetted in triplicate on the bacteria coated agar and incubated 24 hours at 37° C., 5% $CO_2$. Plates were removed from the incubator and the zone of inhibition of bacterial growth were photographed and measured. 10 μg/mL ampicillin was used as a positive control and 2% DMSO/$H_2O$ as a negative control.

The crude peptide post-cleavage was utilized as screening.[49-52] No inhibition zones were observed for some of our peptides, indicating the crude peptide mixture without peptide is not inhibitory. The screening test used the diffusion of the peptides on agar plates to evaluate if the peptides could cause zones of inhibition where the bacteria will not grow. Therefore, a large initial concentration of the peptides could be used to evaluate multiple concentrations of the peptides as the peptide diffuses out into the agar. Ampicillin was used as a positive control antibacterial agent. AMP-1 shows high sequence similarity with AMP-2 and AMP-3 but did not show a zone of inhibition. A homology search of the designed peptide sequences against known peptides or peptide sequences translated from known nucleic acid sequences in the NCBI database was performed as a tblastn search. No significant matches were returned. These peptides do not have homology to previously studied peptides or possibly translated peptides from studied nucleic acids in the NCBI database.

TABLE 6

Inhibition zone of *S. epidermidis* as a screen test of antibacterial activity for candidate novel antimicrobial peptides targeting positively charged sequences. Two of the three candidate peptides, AMP-2 and AMP-3, show antibacterial activity.

| Agent | Sequence | Concentration (mM) | Inhibition Zone (cm) |
|---|---|---|---|
| Ampicillin | n/a | 0.028 | 1.6 |
| APD3 peptide 1 (crude) | DYHHGVRVL (SEQ ID NO: 11) | 0.377 | 0.0 |
| APD3 peptide 2 (crude) | GIHDILKYGKPS (SEQ ID NO: 12) | 0.407 | 1.0 |
| AMP-1 (crude) | ESYKKML (SEQ ID NO: 13) | 0.468 | 0 |
| AMP-2 (crude) | ESYKRMF (SEQ ID NO: 14) | 0.431 | 0.9 |
| AMP-3 (crude) | ESYKHMF (SEQ ID NO: 15) | 0.439 | 1.1 |

TABLE 7

Inhibition zone of *S. epidermidis* as a screen test of antibacterial activity for candidate novel antimicrobial peptides. Underlined letters indicate residues conserved in novel peptides compared to the peptide chosen from APD3, Hp404.

| Agent | Sequence | Concentration (mM) | Inhibition Zone (cm) |
|---|---|---|---|
| Ampicillin | n/a | 0.028 | 1.6 |
| Hp1404 (crude) | GILGKLWEGVK STF (SEQ ID NO: 16) | 2.61 | 2.3 |
| AMP-4 (crude) | ATLGVLWESIR GHR (SEQ ID NO: 17) | 2.51 | 0 |
| AMP-5 (crude) | ATLGVLWEGAR GHT (SEQ ID NO: 18) | 2.73 | 1.2 |
| AMP-6 (crude) | GTLANGWEGVR TNH (SEQ ID NO: 19) | 2.65 | 0 |

Example 3. Spacer Design for Chimeric Peptides for Acrylic Polymeric Surfaces and PolyUrethane Polymeric Surfaces A chimeric antimicrobial peptide for binding an acrylic polymer surface was designed.[53] The method for evaluating the desired secondary structures of the chimeric peptide involved a residue-specific description of secondary structures. The secondary structure features as a function of residue position were determined for a solid binding peptide, PUABP1 (GRAVRRSIRRRV) (SEQ ID NO: 20) [54], and antimicrobial peptide AMP1 (LKLLKKLLKLLKKL) (SEQ ID NO: 8), and a chimeric peptide PUABP1-GSGGG-AMP1.

While there appeared to be similarities in the secondary structure frequencies of the residues in the individual domains that correspond to the chimeric peptide, there were discernable differences. A spacer design scheme that will design spacers that preserve as much of the predicted secondary structure as possible was studied. The Manhattan distance to define the differences between the individual domain frequencies and the chimeric domain as the spacer frequency error (SFE) was used.

$$SFE = \sum_{i=0}^{n} |f_{chimeric\ residue} - f_{domain\ residue}|$$

SFE was calculated by feature category (helical features, beta sheet features, bends and turns, and left/right orientation). These categories were averaged, then summed to calculate the overall spacer frequency error. These calculations were plotted for repetitions of structure generations of 1000 decoys. The solid binding peptide candidates were PUABP1 and PUABP2 (AIRGIRGIRGIR) (SEQ ID NO: 21) and the antimicrobial peptide candidates were AMP1 and AMPa (KWKLWKKIEKWGQGIGAVLKWLTTWL) (SEQ ID NO: 22). The solid binding peptide candidates PUABP1 and PUABP2 both have GSGGG as a highly ranked spacer for either antimicrobial peptide tested. GSGGG (SEQ ID NO: 2) is the top spacer for both antimicrobial peptides for PUABP1 and for the top spacer for PUABP2 and AMPa. The top scoring spacer for PUABP2 and AMP1 was Soluble Alpha Helix 1 (KGSVLSAD) (SEQ ID NO: 23). These rankings may be further improved by reducing the variation of SFE estimates by incorporating more structure decoy sets (current data N=6) or by incorporation larger structure decoy sets whose statistical frequencies of secondary structures converge.

The ranking of the spacers due to the preservation of secondary structures in single domain sequences compared to the chimeric domain sequences is demonstrated herein. It is further shown that the difference in the error is spacer dependent.

Thus, two methods of using structure-function relationships to design spacer sequences between peptide domains are shown. The first method uses the existence of secondary structure of a particular length and the second method uses the existence of a secondary structure feature at a particular position within the sequence to determine the structure description.

Exemplary chimeric peptides for acrylic polymer surfaces and/or polyurethane surfaces are shown in Table 8.

TABLE 8

Exemplary chimeric peptides for acrylic polymer surfaces and/or polyurethane surfaces.

| Peptide | Sequence |
| --- | --- |
| PUABP1-Spacer5-AMP1 | GRAVRRSIRRRV-GSGGG-LKLLKKLLKLLKK (SEQ ID NO: 24) |
| PUABP1-Spacer5-AMPa | GRAVRRSIRRRV-GSGGG-KWKLWKKIEKWGQGIGAVLK WLTTWL (SEQ ID NO: 25) |
| PUABP1-KGSVLSAD-AMP1 | GRAVRRSIRRRV-KGSVLSAD-LKLLKKLLKLLKK (SEQ ID NO: 26) |
| PUABP1-KGSVLSAD-AMPa | GRAVRRSIRRRV-KGSVLSAD-KWKLWKKIEKWGQGIGA VLKWLTTWL (SEQ ID NO: 27) |
| PUABP1-Spacer3-AMP1 | GRAVRRSIRRRV-GGG-LKLLKKLLKLLKK (SEQ ID NO: 28) |
| PUABP1-Spacer3-AMPa | GRAVRRSIRRRV-GGG-KWKLWKKIEKWGQGIGAVLKWL TTWL (SEQ ID NO: 29) |
| PUABP2-Spacer5-AMP1 | AIRGIRGIRGIR-GSGGG-LKLLKKLLKLLKK (SEQ ID NO: 30) |
| PUABP2-Spacer5-AMPa | AIRGIRGIRGIR-GSGGG-KWKLWKKIEKWGQGIGAVLK WLTTWL (SEQ ID NO: 31) |
| PUABP2-KGSVLSAD-AMP1 | AIRGIRGIRGIR-KGSVLSAD-LKLLKKLLKLLKK (SEQ ID NO: 32) |
| PUABP2-KGSVLSAD-AMPa | AIRGIRGIRGIR-KGSVLSAD-KWKLWKKIEKWGQGIGA VLKWLTTWL (SEQ ID NO: 33) |
| PUABP2-Spacer3-AMP1 | AIRGIRGIRGIR-GGG-LKLLKKLLKLLKK (SEQ ID NO: 34) |
| PUABP2-Spacer3-AMPa | AIRGIRGIRGIR-GGG-KWKLWKKIEKWGQGIGAVLKWL TTWL (SEQ ID NO: 35) |

Example 4. Spacer Design for Chimeric Peptides for Calcium Phosphate Surfaces

The same functionalization approach from titanium was applied to calcium phosphate to demonstrate that the technology of displaying antimicrobial peptides and potentially other biological signals is applicable to different types of biomaterials. The main mineral phases of calcium phosphate are amorphous calcium phosphate (ACP), octacalcium phosphate (OCP) and hydroxyapatite (HAP).[55] Like titanium, calcium phosphate is widely used as a biomaterial in orthopedics and dental applications.[56] Calcium phosphate is used as an implant coating because of its osteoinductive and osteoconductive properties in a variety of mineral phases.[56-62] No mineral phase of calcium phosphate has any known antibacterial properties to protect the implant surface from infection. Therefore, due to the risk of surgical site infections, the protection of the calcium phosphate surface against drug-resistant bacteria must go beyond what prophylactic systemic antibiotics provide.[61,63,64] In order to extend the approach from titanium to calcium phosphate, solid binding peptides that have similar binding kinetics for calcium phosphate as the solid binding peptides used as part of the chimeric peptides for titanium were assessed. Solid binding peptides with comparable binding kinetics for the hydroxyapatite surface like the titanium surface were identified. It is demonstrated herein that a hydroxyapatite binding chimeric antimicrobial peptide will show similar antibacterial activity to titanium-binding chimeric antimicrobial peptides and will create antibacterial hydroxyapatite surfaces.

Figure 11A:
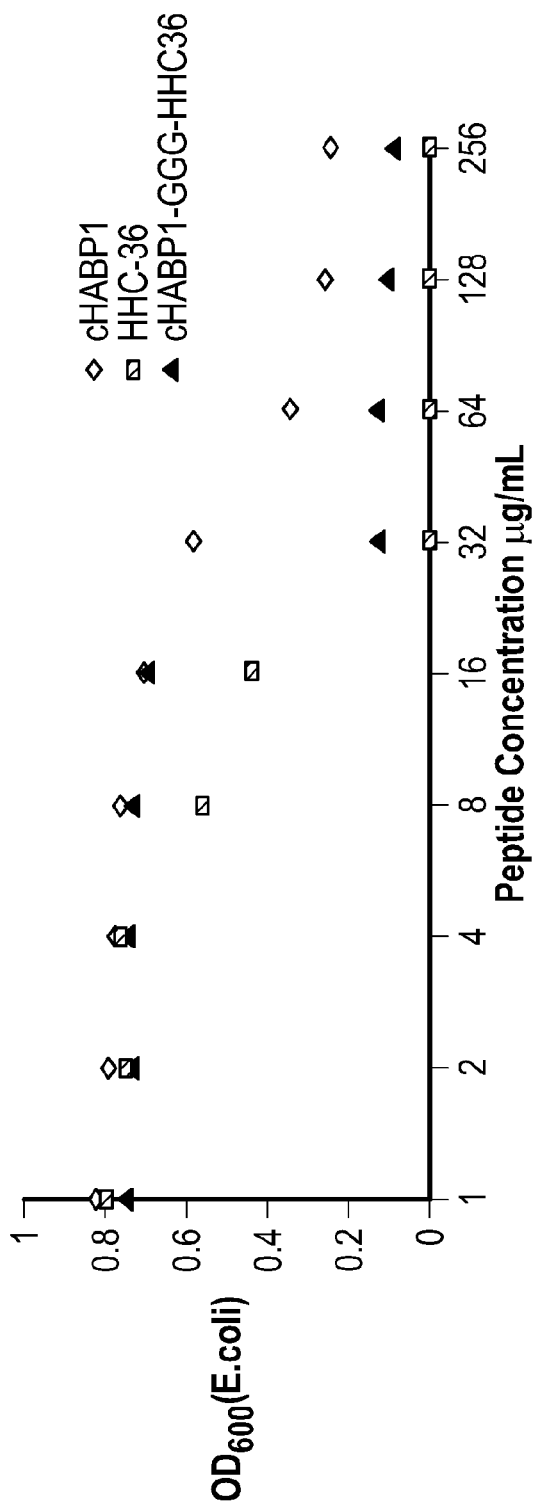
FIG. 11 provides bacterial turbidity as a function of hydroxyapatite binding chimeric peptide concentration and its component domains. Two different pathogens were evaluated. A) *E. coli* can be pathogenic in urinary infections and B) *S. mutans* is a pathogenic bacterial in the oral environment which plays a role in dental caries.
Figure 11B:
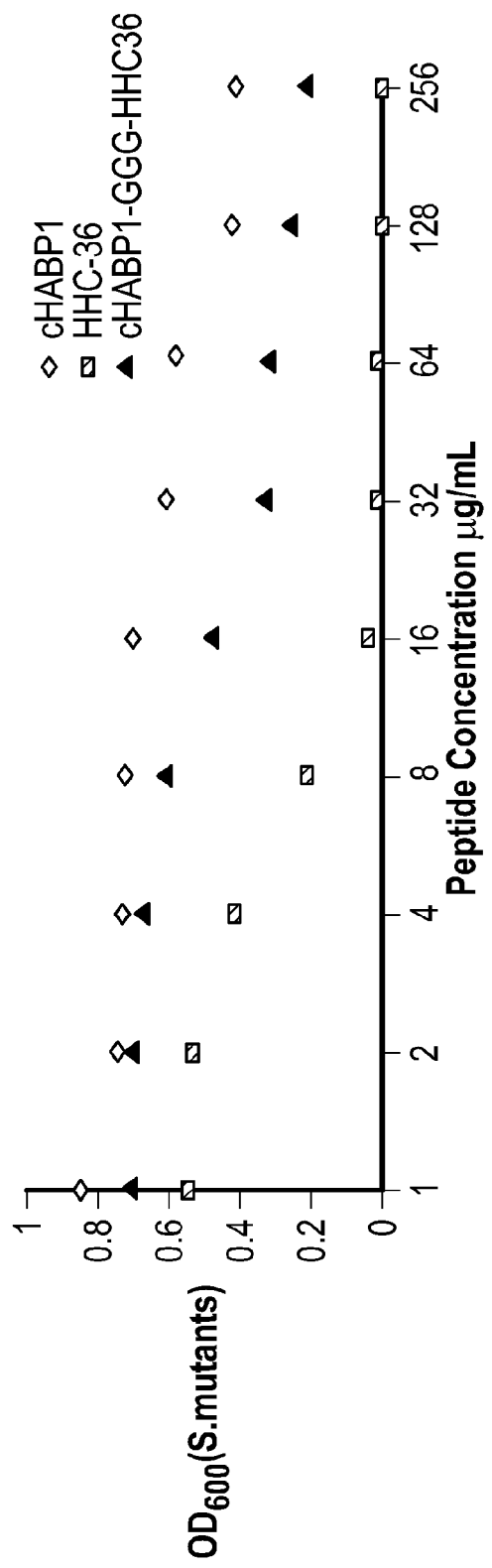

The antibacterial activity against two strains of bacteria of a previously published cHABP1 peptide,[65,66] an antimicrobial peptide designed through artificial intelligence methods (HHC-36),[67] and a chimeric peptide cHABP1-GGG-HHC36 to functionalize calcium phosphate surfaces with antibacterial activity. Table 9 and FIG. 11. Table 9 displays the sequences of the peptides and their estimated minimum inhibitory concentration. MIC values against some *E. coli* strains for HHC-36 have been previously reported, ranging from 2.5 μM-5.4 μM.[67,68] The MIC estimate for a unique strain of *E. coli* (*Escherichia coli*, ATCC® 25922™) is 21.5 μM. In addition to providing an MIC estimate for a gram-positive bacteria, an MIC value for HHC-36 for a gram-negative bacteria, *S. mutans* (10.8 μM) is provided. FIG. 11 shows the results from a MIC assay in a well plate in which larger absorbance values of the well 600 nm implies more bacterial growth because increasing bacteria in a well reduces the transmitted radiant power. At each tested concentration in the assay, HHC-36 resulted in wells with the least absorbance as expected from its known antibacterial activity. The wells with the next least absorbance were the wells with chimeric peptide. Finally, while the cHABP1 peptide wells have the most absorbance and, thus, bacterial growth, the peptide did show some antibacterial activity in the higher tested concentrations

TABLE 9

Antimicrobial activity of peptides for the calcium phosphate surface.

| Peptide Name | Sequence | *S. mutans* IC$_{50}$ | *E. coli* IC$_{50}$ |
|---|---|---|---|
| cHABP1 | CMLPHHGAC (SEQ ID NO: 36) | 128 μg/mL | 48 μg/mL |
| HHC-36 | KRWWKWWRR (SEQ ID NO: 37) | 3 μg/mL | 12 μg/mL |
| cHABP1-GGG-HHC36 | CMLPHHGAC-GGG-KRWWKWWRR (SEQ ID NO: 38) | 16 μg/mL | 18 μg/mL |

Example 5. Spacer Design for Chimeric Peptides for Zirconia Surfaces

Zirconia has been used as a dental implant material for its white, ceramic appearance. In our modular concept, replacing the surface leads to changing the solid-binding peptide.

Spacer sequences which increase targeted secondary structural features for two given peptide domains were discovered. Table 10 shows the MLEM2 inducted rules for selected rules combining the antibacterial activity and structure data from chimeric binding antimicrobial peptides from titanium and calcium phosphate surfaces. The rule that applied to the multiple pathogens is that 5-a.a.-α helices correspond to high antimicrobial activity for the antimicrobial peptide domains tested, AMP1 and AMP2 from Yucesoy et al.[71]

TABLE 10

Selected secondary structure feature rules from the MLEM2 method relating to high antibacterial activity from data mining structure ensembles.

| Secondary Structure Feature | Pathogen | Antibacterial Activity | Ensemble Frequency |
|---|---|---|---|
| 12-a.a.-α helix | *E. coli* | High | 4.2% |
| 11-a.a.-α helix | *E. coli* | High | 3.3% |
| 5-a.a.-α helix | *E. coli/S. mutans* | High | 2.2% |

The initial basis was to start with evaluating the structural frequencies of different kinds of spacers: flexible, putative π helices, and putative a helices, both hydrophobic and hydrophilic. The 5-aa α-Helix Frequency was determined as the average among the chimeric peptides with each of the two antimicrobial peptide domains, AMP1 (LKLLKKLLKLLKKL) (SEQ ID NO: 8) and AMP2 (KWKRWWWWR) (SEQ ID NO: 39), and each of two zirconia-binding domains, ZrBP (RPRENRGRERF) (SEQ ID NO: 40) and ZrBPM1 (RPREQRGRER) (SEQ ID NO: 41).

TABLE 11

5-a.a. α helix frequencies for the initial generation of chimeric spacers. Each frequency is the average of structural ensembles for chimeric peptides having either TiBPS1 or TIBPS2 and either AMP1 or AMP2 domains.

| Spacer | Sequence | 5-aa α-Helix Frequency |
|---|---|---|
| π-Helix 1 Spacer | WLMNYFWPL (SEQ ID NO: 42) | 5.4% |
| π-Helix 2 Spacer | YLMNYLLPY (SEQ ID ON: 43) | 5.0% |
| Soluble α-Helix Spacer 2 | PKSALQEL (SEQ ID NO: 44) | 4.3% |
| Original Spacer | GGG (SEQ ID NO: 1) | 4.0% |

The top feature frequency spacers, shown in Table 11, were selected to cross-over and mutate to form a new generation of spacers more tailored to produce the secondary structure of interest in the novel chimeric peptides. To evaluate the secondary structure feature frequency, the average of four separate chimeric peptide sequences: ZrBPS1-Spacer-AMP1, ZrBPS1-Spacer-AMP2, ZrBPS2-Spacer-AMP1 and ZrBPS2-Spacer-AMP2 was taken. The 5-aa α helix frequencies of the spacers of the initial generation are in Table 11. To form the next generation of spacers, the top half of the initial generation, shown in Table 11, were crossed-over and mutated. The resulting evaluation of 5-aa α helix frequency of selected spacers that have improved frequencies compared to the initial generation is in Table 12.

TABLE 12

Second generation of spacers derived from initial generation of spacers in Table 11.

| Spacer | Sequence | 5-aa α Helix Frequency |
|---|---|---|
| L1I & L5I Soluble AH2 | IGVVISAV (SEQ ID NO: 45) | 7.3% |
| Soluble AH2 × π Helix 2 | KGSVYLLPY (SEQ ID NO: 46) | 7.1% |
| π Helix 1 × Soluble AH2 | WLMNLSAD (SEQ ID NO: 47) | 5.9% |
| Original Spacer | GGG (SEQ ID NO: 1) | 4.0% |

Exemplary chimeric peptides that binds to zirconia surfaces include: ZrBP-IGVVISAV-AMP1: RPRENRGRERF-IGVVISAV-LKLLKKLLKLLKKL (SEQ ID NO: 48); ZrBP-WLMNYFWPL-AMP1: RPRENRGRERF-WLMNYFWPL-LKLLKKLLKLLKKL (SEQ ID NO: 49); ZrBP-YLMNYLLPY-AMP1: RPRENRGRERF-YLMNYLLPY-LKLLKKLLKLLKKL (SEQ ID NO: 50); ZrBP-PKSALQEL-AMP1: RPRENRGRERF-PKSALQEL-LKLLKKLLKLLKKL (SEQ ID NO: 51); ZrBP-GGG-AMP1: RPRENRGRERF-GGG-LKLLKKLLKLLKKL (SEQ ID NO: 52); ZrBP-KGSVYLLPY-AMP1: RPRENRGRERF-KGSVYLLPY-LKLLKKLLKLLKK (SEQ ID NO: 53); ZrBP-WLMNLSAD-AMP1: RPRENRGRERF-WLMNLSAD-LKLLKKLLKLLKKL (SEQ ID NO: 54); and ZrBP-KGSVLSAD-AMP1: RPRENRGRERF-KGSVLSAD-LKLLKKLLKLLKKL (SEQ ID NO: 55).

REFERENCES

1. A. J. Carr et al., The Lancet 379, 1331 (2012).
2. A. S. D. Al-Radha, D. Dymock, C. Younes and D. O'Sullivan, J. Dent. 40, 146 (2012).
3. R. Gugwad, G. S. Reddy, R. G. Reddy, R. Bhatt and S. C. Nagaral, Clin. Dent. 7, 0974 (2013).
4. M. A.-H. Gepreel and M. Niinomi, J. Mech. Behay. Biomed. Mater. 20, 407 (2013).
5. N. C. C. Verissimo et al., J. Biomed. Mater. Res. A, 103, 3757 (2015).
6. E. M. Pritchard, T. Valentin, B. Panilaitis, F. Omenetto and D. L. Kaplan, Adv. Funct. Mater. 23, 854 (2013).
7. M. Zilberman and J. J. Elsner, J. Control. Release 130, 202 (2008).
8. N. M. Bernthal et al., J. Vis. Exp. e51612 (2014).
9. S. Ridgeway et al., J. Bone Joint Surg. Bri. 87, 844 (2005).
10. M. A. Olsen et al., J. Bone Joint Surg. 90, 62 (2008).
11. P. Sadoghi et al., J. Arthroplasty 28, 1329 (2013).
12. A. Rodriguez-Cano, M.-A. Pacha-Olivenza, R. Babiano, P. Cintas and M.-L. Gonzalez-Martin, Surf. Coat. Technol. 245, 66 (2014).
13. S. Peng and Y. Zhu, Chem. Lett. 43, 355 (2014).
14. N. J. Hickok and I. M. Shapiro, Adv. Drug Deliv. Rev. 64, 1165 (2012).
15. C. Ketonis, J. Parvizi and L. C. Jones, J. Am. Acad. Orthop. Surg. 20, 478 (2012).
16. X. Chen et al., Surf. Coat. Technol. 216, 158 (2013).
17. B. Gottenbos, H. C. van der Mei, F. Klatter, P. Nieuwenhuis and H. J. Busscher, Biomaterials 23, 1417 (2002).
18. G. He et al., J. Mater. Chem. B, Mater. Biol. Med. 3, 6676 (2015).
19. D.-J. Lin et al., J. Biomater. Appl. 27, 553 (2013).
20. M. Pasupuleti, A. Schmidtchen and M. Malmsten, Crit. Rev. Biotechnol. 32, 143 (2012).
21. A. L. Hilchie, K. Wuerth and R. E. Hancock, Nat. Chem. Biol. 9, 761 (2013).
22. A. Cederlund, G. H. Gudmundsson and B. Agerberth, Febs J. 278, 3942 (2011).
23. Y. Li, Q. Xiang, Q. Zhang, Y. Huang and Z. Su, Peptides 37, 207 (2012).
24. D. Yucesoy et al., JOM 67, 754 (2015).
25. H. Yazici et al., Acta Biomater. 9, 53415352 (2013).
26. H. Yazici et al., ACS Appl. Mater. Interfaces 8, 5070 (2016).
27. C. Tamerler and M. Sarikaya, Acta Biomater. 3, 289 (2007).
28. C. Tamerler et al., Biopolymers 94, 78 (2010).
29. U. O. Seker et al., Langmuir 23, 7895 (2007).
30. C. D. Fjell, H. Jenssen, W. A. Cheung, R. E. Hancock and A. Cherkasov, Chem. Biol. Drug Des. 77, 48 (2011).
31. Y. Zhou, M. L. Snead and C. Tamerler, Nanomedicine 11, 431 (2015).
32. M. R. Wilkins et al., Methods Mol. Biol. 112, 531 (1999).
33. S. Chaudhury, S. Lyskov and J. J. Gray, Bioinformatics 26, 689 (2010).
34. A. Leaver-Fay et al., Methods Enzymol. 487, 545 (2011).
35. E. F. Pettersen et al., J. Comput. Chem. 25, 1605 (2004).
36. Z. Pawlak, Cybern. Sys. 29, 661 (1998).
37. J. W. Grzymala-Busse and W. Rzasa, Fundam. Inform. 100, 99 (2010).
38. C. Wiedemann, P. Bellstedt and M. G€ orlach, Bioinformatics, 29, 1750 (2013).
39. V. Raussens, J. M. Ruysschaert and E. Goormaghtigh, Anal. Biochem. 319, 114 (2003).
40. S. Socransky, A. Haffajee, J. Lindhe, T. Karring and N. Lang, Clinical Periodontology and Implant Dentistry (Wiley, N.Y., 2008).
41. L. Montanaro et al., Future Microbiol. 6, 1329 (2011).
42. W. C. Wimley, ACS Chem. Biol. 5, 905 (2010).
43. C. D. Fjell, J. A. Hiss, R. E. Hancock and G. Schneider, Nat. Rev. Drug Discov. 11, 37 (2012).
44. H. Choi, N. Rangarajan and J. C. Weisshaar, Trends Microbiol. 24, 111 (2016).
45. M. Li et al., Adv. Health. Mater. 5, 557 (2016).
46. S. N. Rampersad, Sensors (Basel) 12, 12347 (2012).
47. J. W. Costerton, P. S. Stewart and E. P. Greenberg, Science 284, 1318 (1999).
48. Wang G, Li X, Wang Z. APD3: the antimicrobial peptide database as a tool for research and education. Nucleic Acids Research. 2015.
49. Lopez-Perez P M, Grimsey E, Bourne L, Mikut R, Hilpert K. Screening and Optimizing Antimicrobial Peptides by Using SPOT-Synthesis. Frontiers in Chemistry. 2017; 5.
50. Borquaye L S, Darko G, Ocansey E, Ankomah E. Antimicrobial and antioxidant properties of the crude peptide extracts of Galatea paradoxa and Patella rustica. Springerplus. 2015; 4.
51. Bluhm M E C, Knappe D, Hoffmann R. Structure-activity relationship study using peptide arrays to optimize Api137 for an increased antimicrobial activity against Pseudomonas aeruginosa. European Journal of Medicinal Chemistry. 2015; 103:574-82.
52. Minervini F, Algaron F, Rizzello C G, Fox P F, Monnet V, Gobbetti A. Angiotensin I-converting-enzyme-inhibi- 53. S. Kwon, B. Kim, H. Noh, Study of Physical Properties of UV Protective Film with Acrylate Polymers, Polymer-Korea 41(2) (2017) 295-300.
54. D. Carson, M. Hnilova, X. Yang, C. L. Nemeth, J. H. Tsui, A. S. Smith, A. Jiao, M. Regnier, C. E. Murry, C. Tamerler, Nanotopography-induced structural anisotropy and sarcomere development in human cardiomyocytes derived from induced pluripotent stem cells, ACS applied materials & interfaces 8(34) (2016) 21923-21932.
55. S. Mann, Biomineralization: principles and concepts in bioinorganic materials chemistry, Oxford University Press on Demand 2001.
56. S. R. Paital, N. B. Dahotre, Calcium phosphate coatings for bio-implant applications: Materials, performance factors, and methodologies, Materials Science and Engineering: R: Reports 66(1-3) (2009) 1-70.
57. A. Philippart, A. R. Boccaccini, C. Fleck, D. W. Schubert, J. A. Roether, Toughening and functionalization of bioactive ceramic and glass bone scaffolds by biopolymer coatings and infiltration: a review of the last 5 years, Expert Rev Med Devic 12(1) (2015) 93-111.
58. B. J. McEntire, B. S. Bal, M. N. Rahaman, J. Chevalier, G. Pezzotti, Ceramics and ceramic coatings in orthopaedics, Journal of the European Ceramic Society 35(16) (2015) 4327-4369.
59. F. S. Utku, E. Seckin, G. Goller, C. Tamerler, M. Urgen, Electrochemically designed interfaces: Hydroxyapatite coated macro-mesoporous titania surfaces, Applied Surface Science 350 (2015) 62-68.
60. R. A. Surmenev, M. A. Surmeneva, A. A. Ivanova, Significance of calcium phosphate coatings for the enhancement of new bone osteogenesis—A review, Acta biomaterialia 10(2) (2014) 557-579.
61. S. B. Goodman, Z. Yao, M. Keeney, F. Yang, The future of biologic coatings for orthopaedic implants, Biomaterials 34(13) (2013) 3174-3183.
62. R. Z. LeGeros, Properties of osteoconductive biomaterials: calcium phosphates, Clinical orthopaedics and related research 395 (2002) 81-98.
63. J. Raphel, M. Holodniy, S. B. Goodman, S. C. Heilshorn, Multifunctional coatings to simultaneously promote osseointegration and prevent infection of orthopaedic implants, Biomaterials 84 (2016) 301-314.
64. H. Yazici, M. B. ONeill, T. Kacar, B. R. Wilson, E. E. Oren, M. Sarikaya, C. Tamerler, Engineered chimeric peptides as antimicrobial surface coating agents towards infection-free implants, ACS applied materials & interfaces (2016)
65. E. Yuca, A. Y. Karatas, U. O. Seker, M. Gungormus, G. Dinler-Doganay, M. Sarikaya, C. Tamerler, In vitro labeling of hydroxyapatite minerals by an engineered protein, Biotechnol Bioeng 108(5) (2011) 1021-30.
66. M. Gungormus, H. Fong, I. W. Kim, J. S. Evans, C. Tamerler, M. Sarikaya, Regulation of in vitro calcium phosphate mineralization by combinatorially selected hydroxyapatite-binding peptides, Biomacromolecules 9(3) (2008) 966-73.
67. A. Cherkasov, K. Hilpert, H. Jenssen, C. D. Fjell, M. Waldbrook, S. C. Mullaly, R. Volkmer, R. E. W. Hancock, Use of Artificial Intelligence in the Design of Small Peptide Antibiotics Effective against a Broad Spectrum of Highly Antibiotic-Resistant Superbugs, ACS Chemical Biology 4(1) (2009) 65-74.
68. M. Bagheri, S. Arasteh, E. F. Haney, R. E. W. Hancock, Tryptic Stability of Synthetic Bactenecin Derivatives Is Determined by the Side Chain Length of Cationic Residues and the Peptide Conformation, Journal of medicinal chemistry 59(7) (2016) 3079-3086.
69. S. Chaudhury, S. Lyskov, J. J. Gray, PyRosetta: a script-based interface for implementing molecular modeling algorithms using Rosetta, Bioinformatics 26(5) (2010) 689-691.
70. J. J. Gray, S. Chaudhury, S. Lyskov, The PyRosetta interactive platform for protein structure prediction and design: a set of educational modules, Lulu. com 2010.
71. D. Yucesoy, M. Hnilova, K. Boone, P. Arnold, M. Snead, C. Tamerler, Chimeric Peptides as Implant Functionalization Agents for Titanium Alloy Implants with Antimicrobial Properties, JOM 67(4) (2015) 754-766.

Bracketed References

[1] H. Yazici, M. B. O'Neill, T. Kacar, B. R. Wilson, E. E. Oren, M. Sarikaya, C. Tamerler, Engineered Chimeric Peptides as Antimicrobial Surface Coating Agents toward Infection-Free Implants, ACS applied materials & interfaces 8(8) (2016) 5070-81.
[2] M. Gungormus, E. E. Oren, J. A. Horst, H. Fong, M. Hnilova, M. J. Somerman, M. L. Snead, R. Samudrala, C. Tamerler, M. Sarikaya, Cementomimetics-constructing a cementum-like biomineralized microlayer via amelogenin-derived peptides, International journal of oral science 4(2) (2012) 69-77.
[3] M. Gungormus, H. Fong, I. W. Kim, J. S. Evans, C. Tamerler, M. Sarikaya, Regulation of in vitro calcium phosphate mineralization by combinatorially selected hydroxyapatite-binding peptides, Biomacromolecules 9(3) (2008) 966-73.
[4] M. Hnilova, C. R. So, E. E. Oren, B. R. Wilson, T. Kacar, C. Tamerler, M. Sarikaya, Peptide-directed co-assembly of nanoprobes on multimaterial patterned solid surfaces, Soft Matter 8(16) (2012) 4327-4334.
[5] R. Notman, E. E. Oren, C. Tamerler, M. Sarikaya, R. Samudrala, T. R. Walsh, Solution study of engineered quartz binding peptides using replica exchange molecular dynamics, Biomacromolecules 11(12) (2010) 3266-74.
[6] D. Khatayevich, M. Gungormus, H. Yazici, C. So, S. Cetinel, H. Ma, A. Jen, C. Tamerler, M. Sarikaya, Biofunctionalization of materials for implants using engineered peptides, Acta biomaterialia 6(12) (2010) 4634-41.
[7] E. E. Oren, R. Notman, I. W. Kim, J. S. Evans, T. R. Walsh, R. Samudrala, C. Tamerler, M. Sarikaya, Probing the molecular mechanisms of quartz-binding peptides, Langmuir 26(13) (2010) 11003-9.
[8] K. Rübsam, B. Stomps, A. Böker, F. Jakob, U. Schwaneberg, Anchor peptides: A green and versatile method for polypropylene functionalization, Polymer 116 (2017) 124-132.
[9] R. I. Lehrer, A. M. Cole, M. E. Selsted, θ-Defensins: Cyclic Peptides with Endless Potential, J Biol Chem 287(32) (2012) 27014-27019.
[10] Y. Miller, B. Y. Ma, R. Nussinov, Polymorphism in Self-Assembly of Peptide-Based beta-Hairpin Contributes to Network Morphology and Hydrogel Mechanical Rigidity, J Phys Chem B 119(2) (2015) 482-490.
[11] K. Gupta, H. Jang, K. Harlen, A. Puri, R. Nussinov, J. P. Schneider, R. Blumenthal, Mechanism of Membrane Permeation Induced by Synthetic beta-Hairpin Peptides, Biophysical journal 105(9) (2013) 2093-2103.

[12] K. Rajagopal, B. Ozbas, D. J. Pochan, J. P. Schneider, Probing the importance of lateral hydrophobic association in self-assembling peptide hydrogelators, European Biophysics Journal 35(2) (2006) 162-169.

The word "illustrative" is used herein to mean serving as an example, instance, or illustration. Any aspect or design described herein as "illustrative" is not necessarily to be construed as preferred or advantageous over other aspects or designs.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A chimeric peptide comprising an inorganic binding domain having an amino acid sequence selected to bind to an inorganic surface, an antimicrobial domain having an amino acid sequence selected to exhibit antimicrobial activity, and a spacer domain between the inorganic binding domain and the antimicrobial domain, the spacer domain having an amino acid sequence engineered to retain the antimicrobial activity of the antimicrobial domain.

B. The chimeric peptide of Paragraph A, wherein the spacer domain amino acid sequence is selected such that the chimeric peptide exhibits an α-helix feature across the chimeric peptide of less than 20 amino acids.

C. The chimeric peptide of Paragraph A or Paragraph B, wherein the spacer domain amino acid sequence is selected to produce a backbone bend in the chimeric peptide.

D. The chimeric peptide of any one of Paragraphs A-C, wherein the spacer domain amino acid sequence is selected to maximize the percentage of helix frequency over a four amino acid average or a five amino acid average in the chimeric peptide.

E. The chimeric peptide of any one of Paragraphs A-D, wherein the spacer domain amino acid sequence is selected to maximize the amount of non-helical features in the chimeric peptide.

F. The chimeric peptide of any one of Paragraphs A-E, wherein the spacer domain amino acid sequence has less than 10 amino acids.

G. The chimeric peptide of any one of Paragraphs A-F, wherein the spacer domain amino acid sequence has more than 3 amino acids.

H. The chimeric peptide of any one of Paragraphs A-G, wherein the spacer domain amino acid sequence is GSGGG (SEQ ID NO: 2).
I. The chimeric peptide of any one of Paragraphs A-H, wherein the antimicrobial domain amino acid sequence exhibits antimicrobial activity against bacteria associated with clinic implant infections.
J. The chimeric peptide of Paragraph I, wherein the bacteria comprise S. mutans, S. epidermidis, and combinations thereof.
K. The chimeric peptide of any one of Paragraphs A-J, wherein the inorganic surface is selected from titanium, zirconia, zinc, gold, silver, platinum, palladium, alloys thereof, acrylic polymers, polyurethane, or a combination of any two or more thereof.
L. The chimeric peptide of any one of Paragraphs A-K, wherein the inorganic surface is part of an implant.
M. The chimeric peptide of any one of Paragraphs A-L, wherein the inorganic binding domain amino acid sequence is that of a titanium binding peptide, and the antimicrobial domain amino acid sequence is that of an antimicrobial domain exhibiting antimicrobial activity against S. mutans, S. epidermidis, or combinations thereof.
N. The chimeric peptide of any one of Paragraphs A-M, wherein the inorganic binding domain amino acid sequence is RPRENRGRERGL (SEQ ID NO: 7) and the antimicrobial domain acid sequence is LKLLKKLLKLLKKL (SEQ ID NO: 8).
O. The chimeric peptide of any one of Paragraphs A-N, wherein the inorganic binding domain amino acid sequence is selected from the group consisting of RPRENRGRERGL (SEQ ID NO: 7), GRAVRRSIRRRV (SEQ ID NO: 20), AIRGIRGIRGIR (SEQ ID NO: 21), CMLPHHGAC (SEQ ID NO: 36), RPRENRGRERF (SEQ ID NO: 40), and RPREQRGRER (SEQ ID NO: 41); the antimicrobial domain acid sequence is selected from the group consisting of LKLLKKLLKLLKKL (SEQ ID NO: 8), ESYKRMF (SEQ ID NO: 14), ESYKHMF (SEQ ID NO: 15), ATLGVLWEGARGHT (SEQ ID NO: 18), KWKLWKKIEKWGQGIGAVLKWLTTWL (SEQ ID NO: 22), KRWWKWWRR (SEQ ID NO: 37), and KWKRWWWWR (SEQ ID NO: 39); and the spacer domain acid sequence is selected from the group consisting of GGG (SEQ ID NO: 1), GSGGG (SEQ ID NO: 2); KGSVLSAD (SEQ ID NO: 23), WLMNYFWPL (SEQ ID NO: 42), YLMNYLLPY (SEQ ID NO: 43), PKSALQEL (SEQ ID NO: 44), IGVVISAV (SEQ ID NO: 45), KGSVYLLPY (SEQ ID NO: 46), and WLMNLSAD (SEQ ID NO: 47).
P. The chimeric peptide of any one of Paragraphs A-O, wherein the inorganic binding domain amino acid sequence is that of acrylic polymer binding peptide and/or a polyurethane binding peptide, and the antimicrobial domain amino acid sequence is that of an antimicrobial domain exhibiting antimicrobial activity against S. mutans, S. epidermidis, or combinations thereof.
Q. The chimeric peptide of any one of Paragraphs A-P, wherein the inorganic binding domain amino acid sequence is selected from GRAVRRSIRRRV (SEQ ID NO: 20) and AIRGIRGIRGIR (SEQ ID NO: 21); the antimicrobial domain acid sequence is selected from LKLLKKLLKLLKKL (SEQ ID NO: 8) and KWKLWKKIEKWGQGIGAVLKWLTTWL (SEQ ID NO: 22); and the spacer domain amino acid sequence is selected from GGG (SEQ ID NO: 1), GSGGG (SEQ ID NO: 2), and KGSVLSAD (SEQ ID NO: 23).
R. The chimeric peptide of any one of Paragraphs A-Q, wherein the inorganic binding domain amino acid sequence is that of calcium phosphate binding peptide, and the antimicrobial domain amino acid sequence is that of an antimicrobial domain exhibiting antimicrobial activity against S. mutans, S. epidermidis, or combinations thereof.
S. The chimeric peptide of any one of Paragraphs A-R, wherein the inorganic binding domain amino acid sequence is CMLPHHGAC (SEQ ID NO: 36) and the antimicrobial domain acid sequence is KRWWKWWRR (SEQ ID NO: 37).
T. The chimeric peptide of any one of Paragraphs A-S, wherein the inorganic binding domain amino acid sequence is that of zirconia binding peptide, and the antimicrobial domain amino acid sequence is that of an antimicrobial domain exhibiting antimicrobial activity against S. mutans, S. epidermidis, or combinations thereof.
U. The chimeric peptide of any one of Paragraphs A-T, wherein the inorganic binding domain amino acid sequence is selected from RPRENRGRERF (SEQ ID NO: 40) and RPREQRGRER (SEQ ID NO: 41); the antimicrobial domain acid sequence is selected from LKLLKKLLKLLKKL (SEQ ID NO: 8) and KWKRWWWWR (SEQ ID NO: 39); and the spacer domain amino acid sequence is selected from GGG (SEQ ID NO: 1), WLMNYFWPL (SEQ ID NO: 42), YLMNYLLPY (SEQ ID NO: 43), PKSALQEL (SEQ ID NO: 44), IGVVISAV (SEQ ID NO: 45), KGSVYLLPY (SEQ ID NO: 46), and WLMNLSAD (SEQ ID NO: 47).
V. The chimeric peptide of any one of Paragraphs A-U, wherein the inorganic binding domain amino acid sequence is RPRENRGRERGL (SEQ ID NO: 7); the antimicrobial domain acid sequence is LKLLKKLLKLLKKL (SEQ ID NO: 8); and the spacer domain amino acid sequence is selected from: WLMNYFWPL (SEQ ID NO: 42), YLMNYLLPY (SEQ ID NO: 43), PKSALQEL (SEQ ID NO: 44), and KGSVLSAD (SEQ ID NO: 23).
W. The chimeric peptide of any one of Paragraphs A-V, wherein the inorganic binding domain amino acid sequence is RPREQRGERPRP (SEQ ID NO: 56); the antimicrobial domain acid sequence is LKLLKKLLKLLKKL (SEQ ID NO: 8); and the spacer domain amino acid sequence is selected from GGG (SEQ ID NO: 1); GSGGG (SEQ ID NO: 2); WLMNYFWPL (SEQ ID NO: 42), YLMNYLLPY (SEQ ID NO: 43), PKSALQEL (SEQ ID NO: 44), and KGSVLSAD (SEQ ID NO: 23).
X. A chimeric peptide of any one of Paragraphs A-W that is

```
                                            (SEQ ID NO: 9)
RPRENRGRERGLGGGLKLLKKLLKLLKKL;

(SEQ ID NO: 10)
RPRENRGRERGLGSGGGLKLLKKLLKLLKKL;

(SEQ ID NO: 57)
RPRENRGRERGLWLMNYFWPLLKLLKKLLKLLKKL;

(SEQ ID NO: 58)
RPRENRGRERGLYLMNYLLPYLKLLKKLLKLLKKL;

(SEQ ID NO: 59)
RPRENRGRERGLPKSALQELLKLLKKLLKLLKKL;

(SEQ ID NO: 60)
RPRENRGRERGLKGSVLSADLKLLKKLLKLLKKK;
```

RPREQRGERPRPWLMNYFWPLLKLLKKLLKLLKKL; (SEQ ID NO: 61)

RPREQRGERPRPYLMNYLLPYLKLLKKLLKLLKKL; (SEQ ID NO: 62)

RPREQRGERPRPPKSALQELLKLLKKLLKLLKKL; (SEQ ID NO: 63)

RPREQRGERPRPKGSVLSADLKLLKKLLKLLKK; (SEQ ID NO: 64)

RPREQRGERPRPGGGLKLLKKLLKLLKKL; (SEQ ID NO: 65)

RPREQRGERPRPGSGGGLKLLKKLLKLLKKL; (SEQ ID NO: 66)

GRAVRRSIRRRVGSGGGLKLLKKLLKLLKK; (SEQ ID NO: 24)

GRAVRRSIRRRVGSGGGKWKLWKKIEKWGQGIGAVLKWLTTWL; (SEQ ID NO: 25)

GRAVRRSIRRRVKGSVLSADLKLLKKLLKLLKK; (SEQ ID NO: 26)

GRAVRRSIRRRVKGSVLSADKWKLWKKIEKWGQGIGAVLKWLTTWL; (SEQ ID NO: 27)

GRAVRRSIRRRVGGGLKLLKKLLKLLKK; (SEQ ID NO: 28)

GRAVRRSIRRRVGGGKWKLWKKIEKWGQGIGAVLKWLTTWL; (SEQ ID NO: 29)

AIRGIRGIRGIRGSGGGLKLLKKLLKLLKK; (SEQ ID NO: 30)

AIRGIRGIRGIRGSGGGKWKLWKKIEKWGQGIGAVLKWLTTWL; (SEQ ID NO: 31)

AIRGIRGIRGIRKGSVLSADLKLLKKLLKLLKK; (SEQ ID NO: 32)

AIRGIRGIRGIRKGSVLSADKWKLWKKIEKWGQGIGAVLKWLTTWL; (SEQ ID NO: 33)

AIRGIRGIRGIRGGGLKLLKKLLKLLKK; (SEQ ID NO: 34)

AIRGIRGIRGIRGGGKWKLWKKIEKWGQGIGAVLKWLTTWL; (SEQ ID NO: 35)

CMLPHHGACGGGKRWWKWWRR; (SEQ ID NO: 38)

RPRENRGRERFIGVVISAVLKLLKKLLKLLKKL; (SEQ ID NO: 48)

RPRENRGRERFWLMNYFWPLLKLLKKLLKLLKKL; (SEQ ID NO: 49)

RPRENRGRERFYLMNYLLPYLKLLKKLLKLLKKL; (SEQ ID NO: 50)

RPRENRGRERFPKSALQELLKLLKKLLKLLKKL; (SEQ ID NO: 51)

RPRENRGRERFGGGLKLLKKLLKLLKKL; (SEQ ID NO: 52)

RPRENRGRERFKGSVYLLPYLKLLKKLLKLLKK; (SEQ ID NO: 53)

RPRENRGRERFWLMNLSADLKLLKKLLKLLKKL; (SEQ ID NO: 54)
and

RPRENRGRERFKGSVLSADLKLLKKLLKLLKKL. (SEQ ID NO: 55)

Y. The chimeric peptide of any one of Paragraphs A-X, wherein the chimeric peptide is characterized by a minimum inhibitory concentration ($MIC_{CP}$) and the antimicrobial domain amino acid sequence is characterized by a minimum inhibitory concentration ($MIC_{AD}$) and wherein $MIC_{CP}$ is within ±1 fold/100% or less of $MIC_{AD}$.

Z. The chimeric peptide of any one of Paragraphs A-Y, wherein the chimeric peptide is characterized by a minimum inhibitory concentration ($MIC_{CP}$) and wherein the $MIC_{CP}$ is at least 3 times lower than that of a comparative chimeric peptide comprising a spacer domain amino acid sequence of GGG (SEQ ID NO: 1).

AA. The chimeric peptide of any one of Paragraphs A-Z, wherein the chimeric peptide when coated on the inorganic surface provides a surface coverage of selected bacteria of at least 9 times less than the inorganic surface when uncoated.

AB. The chimeric peptide of any one of Paragraphs A-AA, wherein the chimeric peptide when coated on the inorganic surface provides a viability of a selected host cell of at least 40% greater than the inorganic surface when uncoated.

AC. A spacer domain providing a chimeric peptide according to any one of Paragraphs A-AB.

AD. A spacer domain that is GGG (SEQ ID NO: 1); GSGGG (SEQ ID NO: 2); WLMNYFWPL (SEQ ID NO: 42), YLMNYLLPY (SEQ ID NO: 43), PKSALQEL (SEQ ID NO: 44), or KGSVLSAD (SEQ ID NO: 23).

AE. A coated inorganic substrate comprising a layer of the chimeric peptide of any one of Paragraphs A-AB on a surface of an inorganic substrate.

AF. The coated inorganic substrate of Paragraph AE, wherein the inorganic substrate is part of an implant.

AG. A method of making the coated inorganic substrate of Paragraph AE, comprising contacting the inorganic substrate with a solution of the chimeric peptide of any one of Paragraphs A-AB.

AH. A method of using the coated inorganic substrate of Paragraph AE, comprising inserting the coated inorganic substrate into a patient.

Other embodiments are set forth in the following claims, along with the full scope of equivalents to which such claims are entitled.

What is claimed is:

1. A chimeric peptide comprising an inorganic binding domain having an amino acid sequence selected to bind to an inorganic surface, an antimicrobial domain having an amino acid sequence selected to exhibit antimicrobial activity, and a spacer domain between the inorganic binding domain and the antimicrobial domain, the spacer domain having an amino acid sequence engineered to retain the antimicrobial activity of the antimicrobial domain, wherein the chimeric peptide is RPRENRGRERGLGSGGGLKLLKKLLKLLKKL (SEQ ID NO: 10).

2. A coated inorganic substrate comprising a layer of the chimeric peptide of claim 1 on a surface of an inorganic substrate.

3. A method of making the coated inorganic substrate of claim 2, comprising contacting the inorganic substrate with a solution of the chimeric peptide.

* * * * *

SEQUENCE LISTING

```
<160> NUMBER OF SEQ ID NOS: 66

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 1

Gly Gly Gly
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ser Gly Gly Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Val Cys Arg Cys Ile Cys Thr Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Cys Arg Cys Leu Cys Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Lys Val Lys Val Lys Val Lys Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Lys Val Lys Val Lys Val Lys Val
1               5

<210> SEQ ID NO 7

-continued

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Pro Arg Glu Asn Arg Gly Arg Glu Arg Gly Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Lys Leu Leu Lys Lys Leu Leu Lys Leu Leu Lys Lys Leu
1               5                   10

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Pro Arg Glu Asn Arg Gly Arg Glu Arg Gly Leu Gly Gly Gly Leu
1               5                   10                  15

Lys Leu Leu Lys Lys Leu Leu Lys Leu Leu Lys Lys Leu
            20                  25

<210> SEQ ID NO 10
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Pro Arg Glu Asn Arg Gly Arg Glu Arg Gly Leu Gly Ser Gly Gly
1               5                   10                  15

Gly Leu Lys Leu Leu Lys Lys Leu Leu Lys Leu Leu Lys Lys Leu
            20                  25                  30

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Tyr His His Gly Val Arg Val Leu
1               5

<210> SEQ ID NO 12
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Gly Ile His Asp Ile Leu Lys Tyr Gly Lys Pro Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Ser Tyr Lys Lys Met Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Ser Tyr Lys Arg Met Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ser Tyr Lys His Met Phe
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ile Leu Gly Lys Leu Trp Glu Gly Val Lys Ser Thr Phe
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Thr Leu Gly Val Leu Trp Glu Ser Ile Arg Gly His Arg
1               5                   10
```

```
<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Thr Leu Gly Val Leu Trp Glu Gly Ala Arg Gly His Thr
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Thr Leu Ala Asn Gly Trp Glu Gly Val Arg Thr Asn His
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Arg Ala Val Arg Arg Ser Ile Arg Arg Arg Val
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ile Arg Gly Ile Arg Gly Ile Arg Gly Ile Arg
1               5                   10

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Trp Lys Leu Trp Lys Lys Ile Glu Lys Trp Gly Gln Gly Ile Gly
1               5                   10                  15

Ala Val Leu Lys Trp Leu Thr Thr Trp Leu
            20                  25

<210> SEQ ID NO 23
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 23

Lys Gly Ser Val Leu Ser Ala Asp
1               5

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Arg Ala Val Arg Arg Ser Ile Arg Arg Val Gly Ser Gly Gly
1               5                   10                  15

Gly Leu Lys Leu Leu Lys Lys Leu Leu Lys Leu Leu Lys Lys
            20                  25                  30

<210> SEQ ID NO 25
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Arg Ala Val Arg Arg Ser Ile Arg Arg Val Gly Ser Gly Gly
1               5                   10                  15

Gly Lys Trp Lys Leu Trp Lys Lys Ile Glu Lys Trp Gly Gln Gly Ile
            20                  25                  30

Gly Ala Val Leu Lys Trp Leu Thr Thr Trp Leu
            35                  40

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Arg Ala Val Arg Arg Ser Ile Arg Arg Val Lys Gly Ser Val
1               5                   10                  15

Leu Ser Ala Asp Leu Lys Leu Leu Lys Lys Leu Leu Lys Leu Leu Lys
            20                  25                  30

Lys

<210> SEQ ID NO 27
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Arg Ala Val Arg Arg Ser Ile Arg Arg Val Lys Gly Ser Val
1               5                   10                  15

Leu Ser Ala Asp Lys Trp Lys Leu Trp Lys Lys Ile Glu Lys Trp Gly

```
                20                  25                  30

Gln Gly Ile Gly Ala Val Leu Lys Trp Leu Thr Thr Trp Leu
        35                  40                  45

<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Arg Ala Val Arg Arg Ser Ile Arg Arg Val Gly Gly Gly Leu
1               5                   10                  15

Lys Leu Leu Lys Lys Leu Leu Lys Leu Leu Lys Lys
            20                  25

<210> SEQ ID NO 29
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Arg Ala Val Arg Arg Ser Ile Arg Arg Val Gly Gly Gly Lys
1               5                   10                  15

Trp Lys Leu Trp Lys Lys Ile Glu Lys Trp Gly Gln Gly Ile Gly Ala
            20                  25                  30

Val Leu Lys Trp Leu Thr Thr Trp Leu
        35                  40

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Ile Arg Gly Ile Arg Gly Ile Arg Gly Ile Arg Gly Ser Gly Gly
1               5                   10                  15

Gly Leu Lys Leu Leu Lys Lys Leu Leu Lys Leu Leu Lys Lys
            20                  25                  30

<210> SEQ ID NO 31
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Ile Arg Gly Ile Arg Gly Ile Arg Gly Ile Arg Gly Ser Gly Gly
1               5                   10                  15

Gly Lys Trp Lys Leu Trp Lys Lys Ile Glu Lys Trp Gly Gln Gly Ile
            20                  25                  30

Gly Ala Val Leu Lys Trp Leu Thr Thr Trp Leu
        35                  40
```

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 32

Ala Ile Arg Gly Ile Arg Gly Ile Arg Gly Ile Arg Lys Gly Ser Val
1               5                   10                  15

Leu Ser Ala Asp Leu Lys Leu Leu Lys Lys Leu Leu Lys Leu Leu Lys
            20                  25                  30

Lys

<210> SEQ ID NO 33
<211> LENGTH: 46
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 33

Ala Ile Arg Gly Ile Arg Gly Ile Arg Gly Ile Arg Lys Gly Ser Val
1               5                   10                  15

Leu Ser Ala Asp Lys Trp Lys Leu Trp Lys Lys Ile Glu Lys Trp Gly
            20                  25                  30

Gln Gly Ile Gly Ala Val Leu Lys Trp Leu Thr Thr Trp Leu
        35                  40                  45

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 34

Ala Ile Arg Gly Ile Arg Gly Ile Arg Gly Ile Arg Gly Gly Gly Leu
1               5                   10                  15

Lys Leu Leu Lys Lys Leu Leu Lys Leu Leu Lys Lys
            20                  25

<210> SEQ ID NO 35
<211> LENGTH: 41
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 35

Ala Ile Arg Gly Ile Arg Gly Ile Arg Gly Ile Arg Gly Gly Gly Lys
1               5                   10                  15

Trp Lys Leu Trp Lys Lys Ile Glu Lys Trp Gly Gln Gly Ile Gly Ala
            20                  25                  30

Val Leu Lys Trp Leu Thr Thr Trp Leu
        35                  40

<210> SEQ ID NO 36
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Met Leu Pro His His Gly Ala Cys
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Arg Trp Trp Lys Trp Trp Arg Arg
1               5

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Met Leu Pro His His Gly Ala Cys Gly Gly Gly Lys Arg Trp Trp
1               5                   10                  15

Lys Trp Trp Arg Arg
            20

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Trp Lys Arg Trp Trp Trp Trp Arg
1               5

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Pro Arg Glu Asn Arg Gly Arg Glu Arg Phe
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Arg Pro Arg Glu Gln Arg Gly Arg Glu Arg
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Leu Met Asn Tyr Phe Trp Pro Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Leu Met Asn Tyr Leu Leu Pro Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Lys Ser Ala Leu Gln Glu Leu
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Gly Val Val Ile Ser Ala Val
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Gly Ser Val Tyr Leu Leu Pro Tyr
1               5

<210> SEQ ID NO 47
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 47

Trp Leu Met Asn Leu Ser Ala Asp
1               5

<210> SEQ ID NO 48
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Pro Arg Glu Asn Arg Gly Arg Glu Arg Phe Ile Gly Val Val Ile
1               5                   10                  15

Ser Ala Val Leu Lys Leu Leu Lys Lys Leu Leu Lys Leu Leu Lys Lys
            20                  25                  30

Leu

<210> SEQ ID NO 49
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Arg Pro Arg Glu Asn Arg Gly Arg Glu Arg Phe Trp Leu Met Asn Tyr
1               5                   10                  15

Phe Trp Pro Leu Leu Lys Leu Leu Lys Lys Leu Leu Lys Leu Leu Lys
            20                  25                  30

Lys Leu

<210> SEQ ID NO 50
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Arg Pro Arg Glu Asn Arg Gly Arg Glu Arg Phe Tyr Leu Met Asn Tyr
1               5                   10                  15

Leu Leu Pro Tyr Leu Lys Leu Leu Lys Lys Leu Leu Lys Leu Leu Lys
            20                  25                  30

Lys Leu

<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Pro Arg Glu Asn Arg Gly Arg Glu Arg Phe Pro Lys Ser Ala Leu

```
1               5                   10                  15
Gln Glu Leu Leu Lys Leu Leu Lys Lys Leu Leu Lys Leu Leu Lys Lys
            20                  25                  30

Leu

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Pro Arg Glu Asn Arg Gly Arg Glu Arg Phe Gly Gly Gly Leu Lys
1               5                   10                  15

Leu Leu Lys Lys Leu Leu Lys Leu Leu Lys Lys Leu
            20                  25

<210> SEQ ID NO 53
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Arg Pro Arg Glu Asn Arg Gly Arg Glu Arg Phe Lys Gly Ser Val Tyr
1               5                   10                  15

Leu Leu Pro Tyr Leu Lys Leu Leu Lys Lys Leu Leu Lys Leu Leu Lys
            20                  25                  30

Lys

<210> SEQ ID NO 54
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Arg Pro Arg Glu Asn Arg Gly Arg Glu Arg Phe Trp Leu Met Asn Leu
1               5                   10                  15

Ser Ala Asp Leu Lys Leu Leu Lys Lys Leu Leu Lys Leu Leu Lys Lys
            20                  25                  30

Leu

<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Arg Pro Arg Glu Asn Arg Gly Arg Glu Arg Phe Lys Gly Ser Val Leu
1               5                   10                  15

Ser Ala Asp Leu Lys Leu Leu Lys Lys Leu Leu Lys Leu Leu Lys Lys
            20                  25                  30
```

-continued

Leu

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Pro Arg Glu Gln Arg Gly Glu Arg Pro Arg Pro
1               5                   10

<210> SEQ ID NO 57
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Arg Pro Arg Glu Asn Arg Gly Arg Glu Arg Gly Leu Trp Leu Met Asn
1               5                   10                  15

Tyr Phe Trp Pro Leu Leu Lys Leu Leu Lys Leu Leu Lys Leu Leu
            20                  25                  30

Lys Lys Leu
        35

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Arg Pro Arg Glu Asn Arg Gly Arg Glu Arg Gly Leu Tyr Leu Met Asn
1               5                   10                  15

Tyr Leu Leu Pro Tyr Leu Lys Leu Leu Lys Lys Leu Leu Lys Leu Leu
            20                  25                  30

Lys Lys Leu
        35

<210> SEQ ID NO 59
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Arg Pro Arg Glu Asn Arg Gly Arg Glu Arg Gly Leu Pro Lys Ser Ala
1               5                   10                  15

Leu Gln Glu Leu Leu Lys Leu Leu Lys Lys Leu Leu Lys Leu Leu Lys
            20                  25                  30

Lys Leu

<210> SEQ ID NO 60
<211> LENGTH: 33
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 60

Arg Pro Arg Glu Asn Arg Gly Arg Glu Arg Gly Leu Lys Gly Ser Val
1               5                   10                  15

Leu Ser Ala Asp Leu Lys Leu Leu Lys Lys Leu Leu Lys Leu Leu Lys
            20                  25                  30

Lys

<210> SEQ ID NO 61
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Arg Pro Arg Glu Gln Arg Gly Glu Arg Pro Arg Pro Trp Leu Met Asn
1               5                   10                  15

Tyr Phe Trp Pro Leu Leu Lys Leu Leu Lys Lys Leu Leu Lys Leu Leu
            20                  25                  30

Lys Lys Leu
        35

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Arg Pro Arg Glu Gln Arg Gly Glu Arg Pro Arg Pro Tyr Leu Met Asn
1               5                   10                  15

Tyr Leu Leu Pro Tyr Leu Lys Leu Leu Lys Lys Leu Leu Lys Leu Leu
            20                  25                  30

Lys Lys Leu
        35

<210> SEQ ID NO 63
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Arg Pro Arg Glu Gln Arg Gly Glu Arg Pro Arg Pro Pro Lys Ser Ala
1               5                   10                  15

Leu Gln Glu Leu Leu Lys Leu Leu Lys Lys Leu Leu Lys Leu Leu Lys
            20                  25                  30

Lys Leu

<210> SEQ ID NO 64
<211> LENGTH: 33
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 64

Arg Pro Arg Glu Gln Arg Gly Glu Arg Pro Arg Pro Lys Gly Ser Val
1               5                   10                  15

Leu Ser Ala Asp Leu Lys Leu Leu Lys Lys Leu Leu Lys Leu Leu Lys
            20                  25                  30

Lys

<210> SEQ ID NO 65
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Pro Arg Glu Gln Arg Gly Glu Arg Pro Arg Pro Gly Gly Gly Leu
1               5                   10                  15

Lys Leu Leu Lys Lys Leu Leu Lys Leu Leu Lys Lys Leu
            20                  25

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Arg Pro Arg Glu Gln Arg Gly Glu Arg Pro Arg Pro Gly Ser Gly Gly
1               5                   10                  15

Gly Leu Lys Leu Leu Lys Lys Leu Leu Lys Leu Leu Lys Lys Leu
            20                  25                  30